(12) United States Patent
Genin

(10) Patent No.: US 10,166,188 B2
(45) Date of Patent: Jan. 1, 2019

(54) METHOD FOR VACUUM-ASSISTED PRESERVATION OF BIOLOGICS INCLUDING VACCINES

(75) Inventor: Noel Yves Henri Jean Genin, Saint Genis les Ollieres (FR)

(73) Assignee: MERIAL, INC., Duluth, GA (US)

( * ) Notice: Subject to any disclaimer, the term of this patent is extended or adjusted under 35 U.S.C. 154(b) by 29 days.

(21) Appl. No.: 13/485,437

(22) Filed: May 31, 2012

(65) Prior Publication Data

US 2013/0040370 A1    Feb. 14, 2013

Related U.S. Application Data

(60) Provisional application No. 61/490,987, filed on Aug. 12, 2011.

(51) Int. Cl.
| | |
|---|---|
| *C12N 7/04* | (2006.01) |
| *A61K 9/19* | (2006.01) |
| *F26B 5/06* | (2006.01) |
| *C12N 7/00* | (2006.01) |
| *A61K 35/13* | (2015.01) |
| *A61K 35/00* | (2006.01) |
| *A61K 9/00* | (2006.01) |

(52) U.S. Cl.
CPC .................. *A61K 9/19* (2013.01); *C12N 7/00* (2013.01); *F26B 5/06* (2013.01); *A61K 9/0019* (2013.01); *A61K 35/13* (2013.01); *A61K 2035/11* (2013.01); *C12N 2760/18051* (2013.01)

(58) Field of Classification Search
None
See application file for complete search history.

(56) References Cited

U.S. PATENT DOCUMENTS

| | | | |
|---|---|---|---|
| 5,364,756 A * | 11/1994 | Livesey et al. | 435/2 |
| 5,869,306 A | 2/1999 | Kuma et al. | |
| 6,051,238 A | 4/2000 | Volkin et al. | |
| 6,084,074 A | 7/2000 | Kato et al. | |
| 6,231,860 B1 | 5/2001 | Fanget et al. | |
| 6,290,967 B1 | 9/2001 | Volkin et al. | |
| 6,403,098 B1 | 6/2002 | Burke et al. | |
| 6,509,146 B1 * | 1/2003 | Bronshtein | 435/1.3 |
| 6,541,001 B1 * | 4/2003 | Gallili et al. | 424/184.1 |
| 6,872,357 B1 * | 3/2005 | Bronshtein et al. | 422/41 |
| 2005/0106728 A1 * | 5/2005 | Burgess et al. | 435/440 |

(Continued)

FOREIGN PATENT DOCUMENTS

| | | |
|---|---|---|
| EP | 1954308 B1 | 8/2008 |
| WO | WO2007014073 A2 | 2/2007 |
| WO | WO2007038926 A1 | 4/2007 |

OTHER PUBLICATIONS

Shaw et al., "Terminology associated with vitrification and other cryopreservation procedures for oocytes and embryos," Human Reproduction Update vol. 9, No. 6: 583-605 (2003)).*

(Continued)

*Primary Examiner* — Janet L Andres
*Assistant Examiner* — M Franco G Salvoza
(74) *Attorney, Agent, or Firm* — Judy Jarecki-Black; Steffan Finnegan Merial, Inc.

(57) ABSTRACT

The present invention relates generally to the fields of immunology and vaccine technology. More specifically, the present invention relates to methods for vitrifying biological preparations, including peptides, antigens, antibodies, cells, and the like.

20 Claims, 1 Drawing Sheet

(56) References Cited

U.S. PATENT DOCUMENTS

| | | |
|---|---|---|
| 2006/0141483 A1 | 6/2006 | Calton |
| 2008/0050717 A1* | 2/2008 | Brower et al. ................... 435/2 |
| 2008/0206281 A1 | 8/2008 | Look et al. |
| 2010/0015180 A1 | 1/2010 | Francon et al. |
| 2012/0225011 A1* | 9/2012 | Hyde et al. ................. 424/1.11 |

OTHER PUBLICATIONS

Adams et all. Freeze-Drying of Biological Materials. Drying Technology, 9(4), 891-925 (1991).

Matejtschuk et al. Chapter 12. Freeze-Drying of Biological Standards. In: Felix Franks: Freeze Drying/Lyophilization of Pharmaceutical and Biological Products, Jan. 1, 2010 (Jan. 1, 2010), XP009161720; ISBN: 9781439825761.

Tang et al. "Design of Freeze-Drying Processes for Pharmaceuticals: Practical Advice", Pharmaceutical Research, Kluwer Academic Publishers, New York, NY, US, vol. 21, No. 2, Feb. 1, 2004 (Feb. 1, 2004).

\* cited by examiner

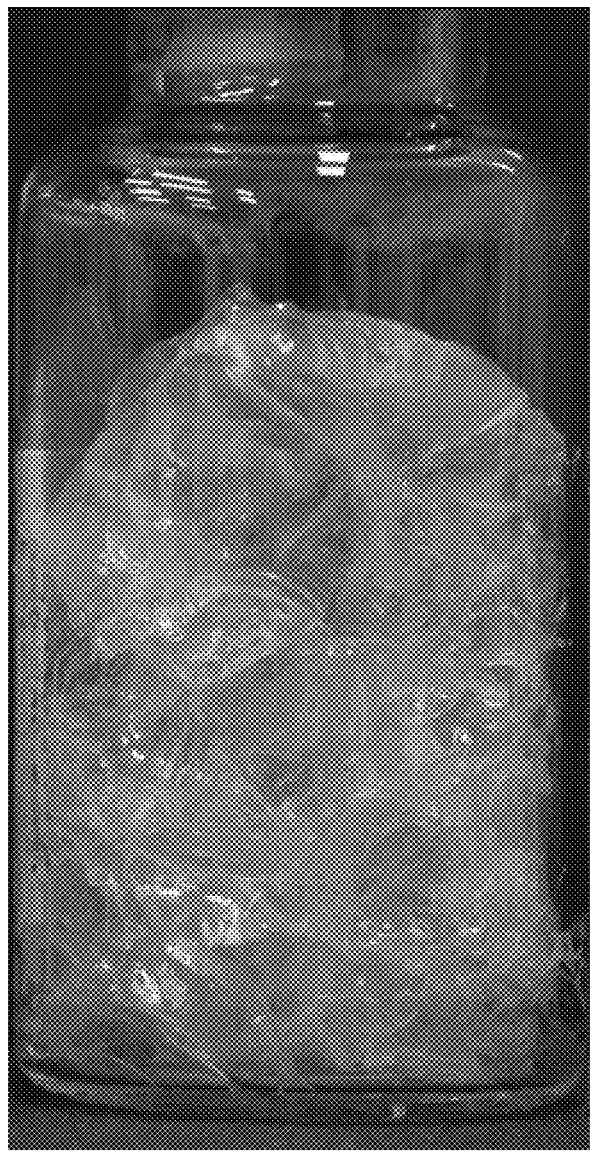

METHOD FOR VACUUM-ASSISTED PRESERVATION OF BIOLOGICS INCLUDING VACCINES

INCORPORATION BY REFERENCE

This application claims priority to provisional application U.S. Ser. No. 61/490,987, filed on May 27, 2011, and incorporated by reference herein in its entirety.

FIELD OF THE INVENTION

The present invention relates generally to the fields of immunology and vaccine technology. More specifically, the present invention relates to stabilizers for freeze-dried live attenuated immunogenic and/or vaccine compositions that may comprise, inter alia, canine paramyxovirus. The invention further relates to stabilized, freeze-dried live attenuated immunogenic and/or vaccine compositions of, for example, canine paramyxovirus, which may contain these stabilizers. Other aspects of the invention are described in or are obvious from the following disclosure, and are within the ambit of the invention.

BACKGROUND OF THE INVENTION

Immunogenic compositions and vaccine compositions comprising biological ingredients, such as viruses, bacteria, parasites, fungi, proteins, polypeptides, glycoproteins, and especially, attenuated live microorganisms, are markedly sensitive to the conditions by which they are prepared, formulated and stored.

Such biological ingredients can be modified and degraded by chemical reactions (e.g. hydrolysis, deamination, Maillard's reaction), many of which are mediated by water. Liquid water allows for molecular movements and can result in modification of protein conformations in compositions comprising biological ingredients. By limiting access to water or by removing water, a major factor of modification and degradation is reduced. Prior methods to confer stability to biological ingredients have primarily involved freezing the water or removing water by freeze-drying.

Lyophilization, or the process of freeze-drying, is a commonly used technique to remove water in the preparation of dehydrated products. Generally, "freeze-drying" an aqueous composition involves three steps. First, the aqueous composition is frozen under conditions of low temperature. Secondly, the frozen water is removed by sublimation under conditions of reduced pressure and low temperature. At this stage, the composition usually contains about 15% water. Third, the residual water is further removed by desorption under conditions of reduced pressure and higher temperatures. At the end of the lyophilization process, a freeze-dried product, also called a "pastille" or "cake" is produced. The freeze-dried product contains very low residual water (from about 0.5% to about 5% weight/weight) and dry material in an amorphous form. This specific state is qualified as "vitreous".

However, substantial loss of immunogenic activity of biological ingredients are observed during the preparation stages, such as before and during lyophilization, and also during storage of immunogenic compositions and vaccine compositions. The integrity of biological ingredients must be safeguarded to ensure that the immunization efficiency of immunogenic compositions and vaccine compositions is retained. The immunogenic activity of biological ingredients is measured by the ability to induce and stimulate an immunologic response when administered to a host or subject.

To limit the manipulation of subjects and the number of administrations, there is a strong need in the art to provide multivalent immunogenic compositions or vaccine compositions. By definition, a multivalent immunogenic composition or vaccine composition comprises more than one active immunogenic component originating from, or derived from, at least two different pathogens. Viruses from different genera can vary in stability during the freeze-drying step and subsequent storage period, resulting in a loss of viability or infectivity. In the case of viruses such as canine paramyxoviruses, the commonly administered active immunogenic components are live attenuated viruses. To efficiently stimulate the immune system, live attenuated viruses must replicate in the immunized subject. Loss of viability or infectivity can occur during the process of freeze-drying multivalent immunogenic compositions or vaccine compositions, during storage of the compositions, or before administration of the compositions after reconstitution. Thus, stabilizers have been added to such freeze-dried compositions. However, to obtain multivalent immunogenic compositions or vaccine compositions that retain their infectivity and/or viability, a common stabilizer that is able to preserve viability and infectivity of different live attenuated pathogens would be particularly advantageous.

Stabilization of biological ingredients in dry form has typically involved the preservation of antitoxins, antigens and bacteria (Flosodort et al (1935) J. Immunol. 29, 389). However, a limitation in this process included partial denaturation of proteins when dried from an aqueous state at ambient temperatures. Drying from the frozen state helped reduce denaturation and led to better, although incomplete, preservation of biological ingredients including bacteria and viruses (Stamp et al. (1947) J. Gen. Microbiol. 1, 251; Rightsel et al. (1967) Cryobiology 3, 423; Rowe et al. (1971) Cryobiology 8, 251).

More recently, sugars such as sucrose, raffinose and trehalose have been added in various combinations as stabilizers prior to lyophilization of viruses. A large number of compounds have been tested for their ability to stabilize different vaccines containing live attenuated biological ingredients, in particular viruses. Such compounds include SPGA (sucrose, phosphate, glutamate, and albumin; Bovarnick et al. (1950) J. Bacteriol. 59, 509-522; U.S. Pat. No. 4,000,256), bovine or human serum albumin, alkali metal salts of glutamic acid, aluminum salts, sucrose, gelatin, starch, lactose, sorbitol, Tris-EDTA, casein hydrolysate, sodium and potassium lactobionate, and monometallic or dimetallic alkali metal phosphate. Other compounds include, for example, SPG-NZ amine (e.g. U.S. Pat. No. 3,783,098) and polyvinylpyrrolidone (PVP) mixtures (e.g. U.S. Pat. No. 3,915,794). Recently, live attenuated flaviviruses have been stabilized using a complex mixture of multiple compounds, including sorbitol, sucrose, optionally trehalose and/or other disaccharide or trisaccharides, urea, and a specific combination of amino acids (US 2010/0015180A1, to Sanofi Pasteur).

Vaccine and immunogenic compositions have had a tremendous impact on public health by reducing morbidity and mortality from a variety of virulent pathogens. However, unintended side effects arising from additives in immunogenic compositions and vaccine compositions continue to pose a potential risk that may outweigh any protective and therapeutic attributes of immunogenic compositions and vaccine compositions.

In the form frequently used in vaccines in the United States, gelatin can provoke serious allergic reactions in about 1 out of 2 million doses. Allergic reactions previously thought to result from albumin (egg protein) are more likely caused by gelatin in the same vaccine. In the case of human serum albumin, while no disease has ever been associated with human serum albumin in vaccines, there is a chance of transmission of a virus through this protein, which is derived from human blood.

Bovine-derived products, such as bovine albumin and gelatin, carries the risk of transmission of CJD (Creutzfeld-Jakob disease, also known as "Mad Cow Disease") through beef blood and connective tissue products used in vaccine manufacturing. However, there have been no reported cases where CJD was transmitted through blood or connective tissue products, the prions that cause CJD have not been found in blood or connective tissue, and the use of bovine-derived products from cows imported from countries where there are known cases of Mad Cow Disease is prohibited. Nevertheless, in view of these risks, efforts have been made to eliminate the use of such products in immunogenic compositions that have been observed to elicit unwanted immune effects.

De Rizzo (de Rizzo et al. (1989) Bull. Pan. Am. Health Organ. 23(3), 299-305) reported freeze-dried measles virus preparations containing sorbitol-gelatin or glutamic acid-lactose solutions. These preparations were stored at −20° C. and their viral titers were determined over a 21 month storage period. The resulting data indicated that the freeze-dried viruses without stabilizer are stable when stored at −20° C. over a period of 21 months. Furthermore, it is well known that freeze-dried measles viruses are stable when stored at −20° C. and can retain potency with virtually no loss for many years (Gray A., (1978) Dev. Biol. Stand. 41, 265-266). However, these results were obtained at −20° C. where freeze-dried measles viruses are stable and do not demonstrate an additional stabilizing effect. These results show only that sorbitol-gelatin and glutamic acid-lactose solutions have no negative effect on the stability of the measles viruses that are stored in freeze-dried form at −20° C.

Precausta (Precausta et al (1980) J. Clin. Microbiol. 12(4), 483-489) examined the effects of residual moisture and sealing atmosphere on the infectivity titer of canine distemper virus (CDV) and infectious bronchitis virus (IBV) after freeze-drying. A lactose solution was added to the preparation of CDV to a final concentration of 75 mg/ml, while the IBV vaccine contained 40 mg of mannitol per ml. When CDV titer before freeze-drying was compared to the titer after freeze-drying and after 12 months of storage at 6° C., the CDV titer is decreased from $10^{1.6}$ to $10^{2.0}$ $CCID_{50}$/ml, which reflects a very significant reduction in CDV titer.

Several methods are known in the art for removing moisture for the purpose of preserving biological preparation. The term "spray-freeze-drying" is understood to mean the spraying with a fluid in a cryogenic environment, followed by freeze-drying of the frozen particles obtained. "Foam-drying" is understood to mean the drying, in the form of a glassy foam, by evaporation of water, of a concentrated solution. And "freeze-foam-drying" is intended to mean the drying, in the form of a glassy foam by sublimation of ice, of a pre-frozen solution, at a temperature below the glass transition temperature and the matrix collapse temperature.

Consequently, there is a need for new stabilizers and methods for preserving viability and infectivity of biological ingredients in freeze-dried form, which are safe and suitable for injection to subjects and which have a good aspect.

Citation or identification of any document in this application is not an admission that such document is available as prior art to the present invention.

SUMMARY OF THE INVENTION

The present invention addresses the need in the art by providing, inter alia, new methods for producing vitrified preparations of biologics including proteins, peptides, antibodies, bacteria, viruses, unicellular parasites, or any human or non-human animal tissue. The viruses may comprise live attenuated canine distemper virus (CDV), canine parainfluenza type 2 (cPi2), canine adenovirus, Marek's disease, Infectious Bursal disease, or Newcastle disease. The bacteria may include *Pasteurella* spp. or *Avibacterium* spp., and biologics may include the KSAC polypeptide of *Leishmania*, In an embodiment, the generalized vitrification method comprises the steps of:

(1) formulating a biologic preparation, including the steps of adding active biologic ingredients, adding stabilizers, which reduce or eliminate damage induced by subjecting biologic ingredients to cryogenic preservation means, including prilling, vitrification, and freeze-drying, and optionally adding one or more adjuvants, which increase the immunogenicity of the biologic in the case of immunological preparations;

(2) filling vials with the biologic preparation of step (1);

(3) loading of vials into temperature-controlled container, wherein the temperature is between −15° C. and 10° C., particularly between −10° C. and 5° C., and even more particularly about 5° C.;

(4) reducing the air pressure of the temperature-controlled container until a pressure within the range of 15-30 mbars is obtained;

(5) maintaining the pressure obtained during step (4) for between 5 and 20 minutes, particularly between 10 and 15 minutes, to allow the temperature of the product to stabilize and to allow volatile gases, including carbonates, to be released from the biologic preparation, wherein the container temperature remains at about 4° C. to about 6° C., or about 5° C. during this step;

(6) decreasing the container air pressure to about 4 to about 7 mbars, or about 5 mbars, for between about 5 to about 20 minutes;

(7) maintaining the pressure of step (6) for about 30 to about 60 minutes, which allows the biologic preparation to become more concentrated;

(8) increasing the temperature of the container from negative to positive temperature (between about 30° C. to about 50° C.) over the course of between 45 and 85 minutes, or about 60 minutes, and holding the pressure constant until reaching about 10° C. to about 20° C., or about 15° C.;

(9) reducing container air pressure to about 1.5 to about 4 mbars, or about 3 mbars, to accelerate the concentration, and until the container temperature reaches and maintains about 30° C. for about 30 minutes to about 90 minutes, or 60 minutes;

(10) further reducing pressure to between about 0.5 and about 4.0 mbars, or about 1 mbar, and maintaining constant pressure until foaming has completed;

(11) further reducing pressure to between about 5 μbar and about 100 μbar, or about 25 μbar, while maintaining the temperature at about 30° C. for about 400 to about 2400 or more minutes, until the desired moisture of between about 0.5% to about 15%, or about 1% to about 4%, is obtained;

(12) stoppering the vials while in the freeze-dryer container, thereby completing the vitrification method.

A person of ordinary skill can carry out the inventive method using any known or yet to be made suitable drying apparatus. Non-limiting examples of a suitable drying apparatus include: 1) a small dryer (one shelf, 200×3 cc vial capacity); 2) a pilot dryer (2 shelves, 3000×3 cc vial capacity), or a large dryer (3 shelves, 10000×3 cc). Routine modifications to the drying apparatus pressure regulation loop may be made such that the freeze-dryer may operate at over a wider range as compared to its usual range.

These and other embodiments are disclosed or are obvious from and encompassed by the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1 shows a photograph of vitrified masses having a cotton candy aspect.

DETAILED DESCRIPTION OF THE INVENTION

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "subject" in the context of the present invention can be a vertebrate, such as a mammal, bird, reptile, amphibian or fish; more advantageously a human, a companion or domesticated animal; a food-producing or feed-producing animal; livestock, game, racing or sport animal such as, but not limited to, bovines, canines, felines, caprines, ovines, porcines, equines, and avians. Preferably, the vertebrate is a canine.

As used herein, "recombinant" refers to a nucleic acid synthesized or otherwise manipulated in vitro (e.g., "recombinant nucleic acid"), to methods of using recombinant nucleic acids to produce gene products in cells, in subjects, or in other biological systems, or to a polypeptide ("recombinant protein") encoded by a recombinant nucleic acid. "Recombinant means" also encompass the excision and ligation of nucleic acids having various coding regions, domains, or promoter sequences from different sources into an expression cassette or vector for, e.g., inducible or constitutive expression of nucleic acid coding sequences.

As used herein, the term "operably linked" means that the components described are in a relationship permitting them to function in their intended manner.

The term "heterologous" when used with reference to a nucleic acid, indicates that the nucleic acid is in a cell, a virus, a subject, or a bacterium where it is not normally found in nature; or comprises two or more nucleic acid subsequences that are not found in the same relationship to each other as normally found in nature, or is recombinantly engineered so that its level of expression, or physical relationship to other nucleic acids or other molecules in a cell, subject, or structure, is not normally found in nature. For instance, a heterologous nucleic acid can be recombinantly produced having two or more sequences from unrelated genes arranged in a manner not found in nature; e.g., a canine gene operably linked to a promoter sequence inserted into, for example, a poxvirus or adenovirus vector. As an example, a heterologous nucleic acid of interest can encode an immunogenic gene product, wherein the heterologous nucleic acid of interest contained in a vector is administered therapeutically or prophylactically as an immunogenic composition or vaccine composition. Heterologous sequences can comprise various combinations of promoters and sequences, numerous examples of which are described in detail herein.

As used herein, a "vector" is a tool that allows or facilitates the transfer of an entity from one environment to another. By way of example, some vectors used in recombinant nucleic acid techniques allow entities, such as a segment of nucleic acid (such as a heterologous nucleic acid segment, such as a heterologous cDNA segment), to be transferred into a target cell. Also used herein is the term "expression vector". The present invention comprehends recombinant vectors that can include, without limitation, viral vectors, bacterial vectors, fungal vectors, protozoan vectors, plasmid vectors, or recombinants thereof.

With respect to heterologous nucleic acids for expression in a vector (e.g., encoding an epitope of interest and/or an antigen and/or immunogen and/or a therapeutic) and documents providing such heterologous nucleic acids, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and all heterologous nucleic acid molecules, promoters, and vectors cited therein can be used in the practice of this invention. In this regard, mention is also made of U.S. Pat. Nos. 6,706,693; 6,716,823; 6,348,450; U.S. patent application Ser. Nos. 10/424,409; 10/052,323; 10/116,963; 10/346,021; and WO99/08713, published Feb. 25, 1999, from PCT/US98/16739.

An "antigen" is a substance that is recognized by the immune system and induces an immune response. The antigen may comprise a whole organism, killed, attenuated or live; a subunit or portion of an organism; a recombinant vector containing an insert with immunogenic properties; a nucleic acid piece or fragment capable of inducing an immune response upon presentation to a host animal; a protein, a polypeptide, a peptide, a glycoprotein, an epitope, a hapten, a carbohydrate, a sugar, or any combination thereof. Alternatively, the antigen may comprise a toxin or antitoxin. A similar term used interchangeably in this context is "immunogen". A "pathogen" refers to a specific causative agent of disease, such as a bacterium, fungus, protozoan, parasite, or virus.

The term "vitrification", as used herein, is intended to mean drying a liquid biological preparation to a low-moisture (e.g. less than about 4%), "cotton candy"-like aspect, using a series of controlled pressure reductions performed for specific lengths of time and over specific ranges of temperature. Vitrification may be carried out in any chamber or container, including a freeze-dryer, wherein the air pressure and temperature can be adjusted to accommodate the ranges presented in the instant disclosure. The term "vitrified composition" and "vitrified preparation" may be used interchangeably, and intended herein to mean any composition, preparation, or formulation that has been subjected to the vitrification method disclosed herein.

As used herein, the terms "immunogenic composition" and "immunological composition" and "immunogenic or immunological composition" cover any composition that elicits an immune response against the antigen or immunogen of interest expressed from vectors; for instance, after administration into a subject, elicits an immune response against the targeted immunogen or antigen of interest. The terms "vaccinal composition" and "vaccine" and "vaccine composition" covers any composition that induces a protective immune response against the antigen of interest, or which efficaciously protects against the antigen; for instance, after administration or injection into the subject, elicits an protective immune response against the targeted antigen or immunogen or provides efficacious protection against the antigen or immunogen expressed from vectors.

As used herein, the term "multivalent" means an immunogenic composition or vaccine composition containing more than one antigen, whether from the same species, from different species, or an immunogenic composition or vaccine composition containing a combination of antigens from different genera.

An "active immunogenic component" in the context of the present invention includes live attenuated pathogens, such as live attenuated viruses, live attenuated bacteria, fungi, or parasites. When the active immunogenic component is part of a multivalent live attenuated CDV and cPi2 immunogenic composition, suspension, or solution of the invention, the active immunogenic component can be advantageously derived from a pathogen other than a paramyxovirus. Also encompassed by the invention are recombinant heterologous immunogens or antigens derived from or originating from one or more pathogens described herein, which can be contained and expressed in, inter alia, viral vectors, bacterial vectors, fungal vectors, and plasmid vectors. The invention also comprehends epitopes of heterologous immunogens or antigens derived from one or more pathogens, immunomodulators such as cytokines, therapeutic agents, toxins, antibodies, antigen-binding fragments of an antibody, adjuvants, or other species such as antisense RNAs, catalytic RNAs, small interfering RNAs, among others.

The term "veterinary composition" means any composition comprising a vector for veterinary use expressing a therapeutic protein as, for example, erythropoietin (EPO) or an immunomodulatory protein, such as, for example, interferon (IFN). Similarly, the term "pharmaceutical composition" means any composition comprising a vector for expressing a therapeutic protein.

The compositions and methods of the present invention can be appropriately applied in the stabilization and vitrification of any biological substance/agent or combination biologic substance/agent plus pharmaceutical/veterinary agent. "Biologics" include, but are not limited to, immunomodulators such as cytokines, therapeutic agents, toxins, antibodies, antigen-binding fragments of an antibody, adjuvants, or other species such as antisense RNAs, catalytic RNAs, small interfering RNAs, among others. After reconstitution of the vitrified materials/substances, these compounds may be used for the prevention of diseases as prophylactic immunization or provide relief against symptoms of disease as therapeutic immunization.

The invention encompasses a method for vitrification of live attenuated immunogenic compositions, which may comprise at least one stabilizer, for example non-reducing sugars or antioxidant compounds. In some embodiments, vitrification stabilizers can optionally comprise at least one non-reducing oligosaccharide and/or at least one bulking agent and/or at least one sugar alcohol. These stabilizers can preserve or assist in retention of the immunogenicity, infectivity, and viability of biological ingredients including, but not limited to, viruses, bacteria, fungi, parasites, proteins, polypeptides, among others. Stabilizers used in the inventive vitrification methods may have a good aspect, including for example, uniform shape and color, and are safe for administration into a subject.

A "reducing monosaccharide" is a saccharide that is able to donate electrons, and thus, able to reduce another compound during oxidation-reduction reactions. Generally, a reducing monosaccharide has aldehyde or ketone groups in its structure. Colorimetric tests are available to identify reducing sugars, such as the Fehling's reagent test (i.e. a solution containing the bistartratocuprate(II) anion, $[Cu(C_4H_4O_6)_2]^{4-}$), which yields a color change from deep blue to red as the copper ion reagent is reduced to the copper metal in presence of a reducing sugar. In the present invention, the reducing monosaccharide preferably comprises glucose, galactose, fructose, mannose, sorbose, or combinations thereof. In one embodiment of the invention, a combination of at least two reducing monosaccharides is provided. The reducing monosaccharides are important for the protection of compositions, notably of proteins and live attenuated pathogens, during the freeze-drying process, particularly during the sublimation step (i.e., first and second desiccation steps), wherein the reducing monosaccharides take the place of the sublimated water and maintain cohesion of the biological structure.

Optionally, sugar alcohols and/or non-reducing oligosaccharides can be added to stabilize preparations vitrified according to the present invention. Combinations of reducing monosaccharides and sugar alcohols, combinations of reducing monosaccharides and non-reducing oligosaccharides, and combinations of reducing monosaccharides, sugar alcohols and non-reducing oligosaccharides are contemplated by the instant disclosure. The sugar alcohol may be, by way of non-limiting example, sorbitol, mannitol, xylitol, or maltitol.

"Non-reducing oligosaccharides" in the context of the invention are sugars comprising from two to ten saccharide units and are unable to reduce another compound during oxidation-reduction reactions. In the present invention, the non-reducing oligosaccharide can be a non-reducing disaccharide or non-reducing trisaccharide, advantageously comprising trehalose, sucrose, or raffinose. The inventive stabilizers can also comprise a mixture of at least two non-reducing oligosaccharides.

An "acid antioxidant" compound is defined as a chemical compound that reacts with and neutralizes oxidants, free radicals (i.e., molecules with unpaired electrons), or chemicals that release free radicals. In the context of the present invention, the antioxidant compound may be in acid form. Acid antioxidants include, but are not limited to, ascorbic acid and/or acidic amino acids, such as aspartic acid and glutamic acid. Combinations of more than one acid antioxidant compound are suitable components of preparations vitrified according to the methods of the instant disclosure.

Bulking agents are also suitable components of compositions vitrified according to the instant disclosure. The bulking agents may be pharmaceutically or veterinarily acceptable polymers such as, but not limited to, dextran, maltodextrin, polyvinylpyrrolidone (PVP), crospovidone, and hydroxyethyl starch. Other non-limiting examples of starch derivatives include microcrystalline cellulose, methyl cellulose, carboxy methyl cellulose, hydroxypropylcellulose, hydroxyethyl methyl cellulose, and hydroxypropyl methyl cellulose. The bulking agents increase the T'g value of the biological compositions, allowing the use of higher temperatures during freezing. The "T'g value" is defined as the glass transition temperature, which corresponds to the temperature below which the frozen composition becomes vitreous. The bulking agent may assist in providing the good aspect observed in the vitrified masses of the instant disclosure, which masses have the general appearance of light, fluffy, cotton candy.

If dextran is used as a bulking agent, its molecular weight can be from about 5000 Da to about 70000 Da, preferably from about 10,000 Da to about 40,000 Da. If PVP is used as a bulking agent, its molecular weight can be from about 8,000 Da to about 360,000 Da, particularly from about 10,000 Da to about 60,000 Da.

If maltodextrin is used as a bulking agent, its dextrose equivalent value (DE, which is a quantitative measure of the degree of starch polymer hydrolysis) can be from about 3 to about 20, preferably from about 5 to about 18, more preferably from about 10 to about 15. If hydroxyethyl starch is used as a bulking agent, its molecular weight can be from about 70,000 Da to about 450,000 Da, preferably from about 130,000 Da to about 200,000 Da. The degree of substitution of hydroxyethyl starch can be from about 0.4 to about 0.7, particularly from about 0.4 to about 0.6. The degree of substitution is defined as the number of hydroxyethyl group per glucose unit.

Some components, including stabilizers, of the biological preparations may be not be readily soluble. However, it is well within the reach of the skilled person to substitute suitably analogous components (e.g. by selecting a more soluble component) and/or to adapt the amounts or quantities of the insoluble component present in the stabilizer for the purpose of obtaining a soluble stabilizer. The solubility of a component can be easily checked by a visual solubility test. A solubility test comprises the steps of adding all of the components of the stabilizer at a temperature of about 55° C., and mixing for about 30 minutes. After approximately 24 hours at room temperature and without any agitation, the stabilizer can be visually checked for appearance of precipitates. If the stabilizer is transparent or limpid, then all the components of the stabilizer are soluble.

Biological preparations vitrified according to the instant disclosure may contain any number of stabilizers. Table 1 provides several examples. "Dextran" comprises dextran-40,000 having a molecular weight of 40,000 Da.

TABLE 1

Compositions of the stabilizers

| Stabilizers | Reducing monosaccharide(s) or mixture | Acid antioxidant | Bulking Agent | Solvent |
| --- | --- | --- | --- | --- |
| F2 | Glucose (5% w/v) Raffinose (5% w/v) | aspartic acid (0.50% w/v) | Dextran (10% w/v) | Water for injection (q.s. 100% v/v) |
| F2B | Glucose (3% w/v) Raffinose (3% w/v) | aspartic acid (0.20% w/v) | Dextran (6% w/v) | Water for injection (q.s. 100% v/v) |
| F6B | Galactose (3% w/v) Mannitol (6% w/v) | aspartic acid (0.40% w/v) | — | Water for injection (q.s. 100% v/v) |
| F33 | Glucose (5% w/v) Fructose (5% w/v) | aspartic acid (0.50% w/v) | Dextran (10% w/v) | Water for injection (q.s. 100% v/v) |
| F37 | Glucose (5% w/v) Raffinose (5% w/v) Sorbitol (10% w/v) | aspartic acid (0.50% w/v) | — | Water for injection (q.s. 100% v/v) |
| A | Glucose (1% w/v) Galactose (5% w/v) | aspartic acid (0.50% w/v) | Dextran (6% w/v) | Water for injection (q.s. 100% v/v) |
| H | Glucose (5% w/v) Raffinose (5% w/v) | aspartic acid (0.50% w/v) | Dextran (6% w/v) | Water for injection (q.s. 100% v/v) |
| K | Glucose (5% w/v) Sucrose (1% w/v) | aspartic acid (0.50% w/v) | Dextran (6% w/v) | Water for injection (q.s. 100% v/v) |
| U | Glucose (1% w/v) Galactose (1% w/v) | aspartic acid (0.50% w/v) | Dextran (6% w/v) | Water for injection (q.s. 100% v/v) |

Also provided by the disclosure is a vitrified immunogenic composition, which is produced by first producing an immunogenic suspension or solution comprising a live attenuated virus, such as but not limited to paramyxovirus, followed by vitrification of same according to the methods of the instant disclosure. The canine paramyxovirus may comprise inter alia canine distemper virus (CDV) and canine parainfluenza type 2 virus (cPi2), both in the form of live attenuated viruses.

In an embodiment, the instant disclosure encompasses vitrified live attenuated paramyxoviruses, in particular, canine paramyxoviruses. The canine paramyxovirus is a virus of the Paramyxoviridae family, which includes canine distemper virus (CDV) and canine parainfluenza type 2 virus (cPi2). Canine paramyxoviruses are responsible for a wide variety of diseases in many species of carnivores, in particular domestic animals, such as dogs, or non-domestic animals, such as ferrets, lions, tigers and leopards.

In the context of the instant disclosure, the term "bulk vaccine composition" is intended to mean a composition which exits the final stage of the antigen production, purified or nonpurified, monovalent, or after multivalent mixing. The term "a dry vaccine composition" is intended to mean a composition of which the residual water content is less than or equal to about 4%, or about 3%, and which is ready to be reconstituted with an aqueous solution in order to be used as a vaccine or directly in dry particulate form. The dry vaccine composition may also be ground and formulated with appropriate excipients, including binders, to produce orally suitable dosage units, for example, tablets and pills.

The present invention also relates to a method for stabilizing one or more live attenuated paramyxovirus. At the final stage in the production of the live attenuated paramyxoviruses (for example, culture on cells, infection and viral culture followed by purification in one or more steps), the purified or nonpurified and concentrated or nonconcentrated viral harvest comprising a live attenuated paramyxovirus is diluted by adding stabilizer, followed by vitrification.

A live attenuated vaccine or immunogenic composition has the following advantages: it can be administered in low doses, particularly if it is self-replicating; it closely mimics the natural/wild-type infection in a subject, and it provides to the subject all possible immunologically important antigens at the same time, i.e., in a single administration.

It is generally agreed that immunogenic compositions or vaccine compositions based on live attenuated microorganisms have the ability to induce a highly effective type of immune response. Such immunogenic compositions or vaccine compositions have the advantage that, once the animal host has been immunized, entry of the pathogen into the host induces an accelerated recall of earlier, cell-mediated or humoral immunity, which is able to control the further growth of the organism before the infection can assume clinically significant proportions. Immunogenic compositions or vaccine compositions based on a killed pathogen (killed vaccine) are generally conceded in the art to be unable or less likely to achieve this type of response. However, immunogenic compositions or vaccine compositions that contain a live pathogen, depending on the level of attenuation, present the danger that the immunized host, upon immunization, can contract the disease against the protection is being sought. Therefore, immunogenic compositions or vaccine compositions that possess the immunizing attributes of a live pathogen, but that is incapable of causing undesirable side effects upon administration to a subject would be highly desirable.

Live attenuated pathogens can be generated by incorporating a broad range of mutations, including single nucleotide changes, site-specific mutations, insertions, substitutions, deletions, or rearrangements. These mutations may affect a small segment of the pathogen's genome, e.g., 15 to 30 nucleotides, or large segments of the pathogen's genome, e g., 50 to 1000 nucleotides, depending on the nature of the mutation. For example, mutations can be introduced upstream or downstream of a pathogen's non-coding regulatory region or element to ablate or impair its activity, thereby resulting in an attenuated phenotype.

Mutations of non-coding regulatory regions of the pathogen's genome, which can result in downregulation of replication of a pathogen's gene, and/or downregulation of transcription of a pathogen's gene can result in the production of defective pathogens in each round of replication; i.e. pathogens containing less than the full complement of genomic regions or segments required for a fully infectious pathogen. Therefore, the altered pathogen will demonstrate attenuated characteristics in that the pathogen will give rise to more defective pathogens than wild type pathogens in each round of replication. However, since the amount of protein, antigen, or immunogen synthesized in each round is similar for both wild type pathogen and the defective pathogen, such attenuated pathogens are likely to be capable of inducing a good immune response in a subject.

Where the pathogen's gene encodes a structural protein, e.g., in the case of pathogens such as viruses, a capsid, matrix, surface or envelope protein, the number of particles produced during replication will be reduced such that the mutated pathogen demonstrates attenuated characteristics; e.g., a titer which results in subclinical levels of infection. For example, a decrease in viral capsid expression will reduce the number of nucleocapsids packaged during replication, whereas a decrease in expression of the envelope protein may reduce the number and/or infectivity of progeny virions. Alternatively, a decrease in expression of the viral enzymes required for replication, e.g., the polymerase, replicase, helicase, and the like, should decrease the number of progeny genomes generated during replication. Since the number of infectious particles produced during replication is reduced, the altered viruses demonstrate attenuated characteristics. However, the number of antigenic virus particles produced will generally be sufficient to induce a vigorous immune response in a subject.

An alternative way to engineer attenuated pathogens involves the introduction of an mutation, including, but not limited to, an insertion, deletion or substitution of one or more amino acid residues and/or epitopes into one or more of the pathogen's proteins. This can be readily accomplished by engineering the appropriate mutation into the corresponding gene sequence of the pathogen. Any change that alters the activity of the pathogen's protein so that replication is modified or reduced is encompassed by the present invention.

For example, in the context of attenuated viruses, mutations that interfere with but do not completely abolish viral attachment to host cell receptors and ensuing infection can be engineered into viral surface antigens or viral proteases involved in processing to produce an attenuated strain. Viral surface antigens or virulence factors can be modified to contain insertions, substitution or deletions of one or more amino acids or epitopes that interfere with or reduce the binding affinity of the viral antigen for the host cell receptors. This approach offers an added advantage in that a chimeric virus, which expresses a foreign or heterologous epitope can be produced, which also demonstrates attenuated characteristics. Such viruses are ideal candidates for use as live recombinant vaccines.

Mutations engineered into any of the viral enzymes include, but are not limited to, insertions, deletions and substitutions in the amino acid sequence of the active site of the enzyme. By way of example, the binding site of an enzyme could be altered such that its binding affinity for its substrate is reduced, and as a result, the enzyme is less specific and/or efficient. For example, a target of choice is the viral polymerase complex, since temperature sensitive mutations exist in all polymerase proteins. Therefore, changes introduced into the amino acid positions associated with such temperature sensitivity can be engineered into the viral polymerase gene so that an attenuated viral strain is produced.

CDV is an enveloped single-stranded RNA virus of about 100-300 nm in diameter and belonging to the genus *Morbillivirus*. The CDV virion core contains a nucleoprotein (NP) peptide that closely associated with viral RNA. A second core peptide is a phosphoprotein (P). The CDV envelope contains three peptides, M protein (matrix protein) and two glycoproteins. The glycoproteins are the hemagglutinin glycoproteins (H) and a fusion (F) glycoprotein. The fusion glycoprotein is degraded into smaller subunits, designated $F_1$ and $F_2$. The H protein is primarily responsible for viral adsorption to target cells and the fusion glycoprotein is responsible for the cell-to-cell fusion. To date, all known distemper virus isolates contain these common viral polypeptides. The route of infection to the dog is by infective aerosol droplets, and transmission of the virus is facilitated by coughing, sneezing and close confinement in a warm, humid, closed environment. Studies suggest that viral infection occurs first in the respiratory epithelium of the upper oronasal tract with subsequent spread to the deep pulmonary parenchyma (Gorham "Canine Distemper", (1960) Advance Veterinary Science, Brandley and Jungher Editors, 6: 288-315).

Tissue macrophages and monocytes located in or along the respiratory epithelium in tonsils appear to be the first cell type to pick up and replicate CDV. The virus then is spread in the bloodstream to distant lymphoreticular tissues. This is accomplished by viremia and occurs anywhere from two to four days after initial infection. Between eight and nine days after infection, the virus spreads beyond lymphoreticular tissues to involve epithelial and mesenchymal tissues (Appel, (1969) Am. J. Vet. Res. 30, 1167-1182). It is at this stage of viral infection that specific host immune responses to viral antigens influence the outcome of disease. The acute fatal form of the disease is characterized by unrestricted viral spread to virtually every tissue in the body. Virus can be found in every excretion and secretion in the infected subject, and by using immunofluorescence methods or antigen tracing techniques, the presence of antigen can be observed in virtually every cell type within the dog. For most of these animals, the most likely cause of death is fulminant fatal neurologic involvement and/or encephalitis.

Some CDV infected dogs exhibit clinically delayed progression of disease and modest convalescent immune responses. Clinical signs, if present, are subtle early in the disease and are a reflection of viral persistence within the central nervous system (CNS). Subsequent development over CNS disease is variable. Most CDV infected dogs exhibit essentially no overt clinical signs of disease and are recognized as convalescent, clinically normal dogs. Actively infected dogs that eventually recover from CDV infection have been shown to demonstrate free circulating anti-viral antibodies on or about post infection day six or seven (Krakowka, et al., (1975) J. Infect. Dis. 132, 384-392). Titers rise rapidly to high levels in early convalescence.

Dogs affected acutely with CDV show variable degrees of depression, anorexia, and fever. The skin may be variably dehydrated, dry-roughened, and inelastic. A proportion of these animals show photophobia and evidence of mucopurulent ocular-nasal discharge. Intermittent diarrhea is a common clinical sign. During this acute viremic phase of the disease, virus is shed in every secretion and excretion. As the disease progresses, pneumonia, frequently due to secondary bacterial invaders, may develop. Dogs in this stage of disease are moderately to severely lymphopenic, depending on the degree or amount of secondary infection. Although acutely affected dogs can show virtually every combination of neurological signs, in its most common presentation, a dog presents petit mal or grand mal seizures. These convulsive episodes occur over time and with increasing frequency.

The second neurologic form of canine distemper is that which occurs with old dog encephalitis (ODE), or occurs after sub-clinical infection and apparent recovery. The CNS signs can be extremely varied in presentation and can be mistaken for brain tumor, head trauma, bacterial meningitis, hydrocephalus, and spinal cord disc disease. A major non-neural manifestation of CDV infection in dogs is CDV-associated immunosuppression (Krakowka, et al., (1980) Am. J. Vet. Res. 41, 284-292). Many of the signs of canine distemper virus infection are attributable to coincidental secondary infectious processes occurring in this debilitated animal.

The disease in dogs can also associated with bacterial pathogens, such as pneumonic bacterial species including, but not limited to, *Bordetella bronchiseptica, Pasteurella* species, *Staphylococcus* and *Streptococcus* species These bacteria are responsible for the purulent conjunctivitis, rhinitis, and bronchopneumonia noted clinically in CDV-infected dogs. Mixed viral infections, chiefly of the respiratory type, also are common. In addition to canine adenovirus II infection, reovirus, canine parainfluenza virus, and presumably other viruses such as canine herpes virus, can all be involved in dual or multiple mixed infections.

cPi2 is an RNA virus that induces a respiratory disease that is one of the most commonly encountered viral diseases of the dog. When the combination of parainfluenza virus, canine adenovirus-2 and the bacteria *Bordetella bronchiseptica* occur together, "kennel cough" results. cPi2 also causes tracheobronchitis that, in some animals, results in exudative pneumonia. Signs of cough develop 7 to 9 days after exposure to the virus. The clinical signs are mild and of short duration unless secondary infections occur.

cPi2 is a spherical enveloped virus with an average diameter of 150-200 nm, with a helical nucleocapsid surrounded by a lipid bilayer covered with glycoprotein spikes. Each virus particle contains a single-stranded, nonsegmented, negative-sense RNA genome with nucleoprotein (NP) and phosphoprotein (P) and large (L) proteins. cPi2 infection is acquired through inhalation of infected respiratory droplet nuclei. The nose and the nasopharynx are the primary sites of infection. The virus initiates infection primarily by attaching to the ciliated epithelial cells of these areas through hemagglutinin-neuraminidase proteins, which specifically combine with neuraminic acid receptors in the host cells. Subsequently, the viruses enter the cell via fusion with the cell membrane mediated by F1 and F2 receptors. The viruses multiply and invade other cells both intracellularly and extracellularly. Virus multiplication occurs throughout the tracheobronchiolar tissues, causing enhanced production of mucus.

Laryngotracheitis is an inflammation of larynx and trachea which, when it occurs in dogs, is known commonly as "kennel cough". The main symptom is cough manifested by a short, dry "hack" or by a series of such coughs. At its most severe, the cough may be paroxysmal, and the infection involves the entire respiratory tract, often producing pneumonia. The cough is also characterized as being deep, persistent, non-productive, and generally accompanied by running eyes and nose. The temperature may be normal, although it is generally elevated. The onset of the disease can be sudden and can occur without preliminary signs. Since the disease is very contagious, infected dogs should be isolated to prevent infection of entire populations. The disease produces major economic losses to kennel owners, and while not usually fatal, it may so weaken dogs as to produce serious effects from other diseases.

Live cPi2 virus and other viruses, such as CDV, canine adenovirus Type 2 (CAV2), and canine parvovirus (CPV) can be propagated in animal tissue cultures until both viruses are rendered non-pathogenic, i.e., the viruses are rendered inactive or otherwise attenuated. The cPi2 virus is capable of propagation in a wide variety of tissue culture systems, such as, for example, chick embryo, duck embryo, porcine kidney, porcine testes, embryonic bovine kidney, feline kidney, canine kidney and monkey kidney; and also in established cell lines, such as, for example, Madin Darby bovine kidney (MDBK), Madin Darby canine kidney (MDCK) and Serum Institute rabbit cornea (SIRC).

For the propagation of, for example, canine adenovirus Type 2 (CAV2), kidney tissue cultures are preferred, particularly those derived from bovines and canines, since CAV2 does not favorably replicate in other animal tissue culture systems as does the cPi2 virus. Attenuation of each virus can be accomplished by standard serial passages, including terminal dilution passage techniques, wherein a sufficient number of passages in a susceptible tissue culture can be employed until the virus is rendered non-pathogenic without loss of immunogenicity. An immunogen, immunogenic composition, or immunogenic suspension or solution prepared therefrom can stimulate an immune response in dogs susceptible to disease without producing the clinical symptoms normally due to the virulent agent to any significant degree. The propagation can be conducted in the same or different tissues as those described above.

The passage time intervals should sufficiently allow the virus to replicate between passages, and incubation temperatures are preferably maintained from about 30° C. to about 38° C. The optimum passage time interval depends on the particular culture system and temperature being employed. In any event, whether or not sufficient replication of the virus has occurred can readily be determined by standard techniques such as the hemadsorption technique described in Shelokov, A. (1958) Proc. Soc. Exp. Biol. Med. 97, 802; which is particularly useful for the cPi2 virus, or by cytopathic observations, such as by allowing the virus to grow during a particular passage prior to the point where a gross cytopathic effect can be observed while continuing incubation.

An advantageous method of propagation utilizes canine kidney cells, particularly continuous MDCK cell lines. For example, for immunogenic or vaccine purposes, about at least 15 and preferably from about 20 to about 45 passages from isolation through dog kidney tissue cultures of the viruses can be made at approximately three-day intervals and at incubation temperatures of about 30 to about 38° C. It is preferred to use the higher passage material, since this will benefit the production of favorable immune responses in subjects in need thereof.

In preparing the immunogenic compositions or vaccine compositions, virulent CDV can be grown in cultured mammalian cells in conventional virus growth conditions. The host cells may be seeded with virus at the time of cell planting, or with a CDV-containing media change when the cell monolayer is 90-100% confluent. The multiplicity of infection (MOI) ratio may be from about 0.001 to about 0.05, preferably about 0.01. Any appropriate mammalian cell growth medium, such as, but not limited to, Eagle's Minimum Essential Medium, Dulbecco's Modified Eagle's Medium, Iscove's Modified Dulbecco's Medium, Ham's F12 medium, F15 medium, RPMI 1640 medium, containing animal serum, such as fetal calf serum, calf serum, horse serum, canine serum and the like, at from about 0% to about 10%, supplements such as L-glutamine and other amino acids both essential and non-essential, Hanks Balanced Salt Solution (HBSS), Earle's salt solution, sodium pyruvate, sodium bicarbonate, insulin, transferrin, and antibiotics and antimycotic agents, such as but not limited to, gentamicin, penicillin, streptomycin, polymyxin B, amphotericin, and FUNGIZONE®, can be used to produce the virus or viruses. Also comprehended by the present invention are serum-free cell culture media.

Infected cell cultures maintained in a temperature range of from about 35° C. to about 40° C. for from about 2 to about 7 days post-seeding, at which time virus can be harvested. The infected cultures may be inoculated with cell growth medium, which may be harvested after an additional incubation period of 2 to 5 days. Virus fluids are harvested into sterile containers and may be clarified by filtration. The virus fluids can be further concentrated using conventional ultrafiltration technology (e.g., Millipore Pellicon systems) with filters having particle size exclusion limits of $10^5$ Daltons.

Other live attenuated viruses that can be mixed with the stabilizers of the present invention include, without limitation, Rabies viruses, Influenza viruses, Parainfluenza viruses, Mumps virus, Adenoviruses such as Canine Adenovirus Type 2 (CAV2), Respiratory syncytial virus, Epstein-Barr virus, Rhinoviruses, Poxviruses such as vaccinia virus, swinepox, raccoonpox, avipoxviruses such as fowlpox, canarypox, dovepox, pigeonpox, Polioviruses, Coxsackieviruses, Echoviruses, Coronaviruses, Rubeola virus, Rubella virus, Varicella-zoster virus, Herpes viruses (human and animal), Herpes simplex virus, Parvoviruses such as canine parvovirus (CPV), Cytomegalovirus, Hepatitis viruses such as Canine contagious hepatitis virus, Human papillomavirus, Alphaviruses such as Semliki Forest Virus, Sindbis Virus, Ross River Virus, Eastern equine encephalitis virus, Western equine encephalitis virus, Venezuelan equine encephalitis virus, O'nyong-nyong virus, Flaviviruses such as dengue fever virus and West Nile Virus, Bunyaviruses, Adenoviruses, Rotaviruses, Hepadnaviruses such as Orthohepadnaviruses and Avihepadnaviruses, Filoviruses, Retroviruses such as porcine endogenous retrovirus, HTLV-1, HTLV-2, FeLV, BLV, MLV, MMSV, Mason-Pfizer monkey virus, Lentiviruses such as HIV-1, HIV-2, FIV, SIV, BIV, Feline calicivirus, Feline panleukopenia virus, Feline infectious peritonitis virus, Feline rhinotracheitis virus, TGE virus (swine), and Foot and mouth disease virus.

The immunogenic compositions or suspensions or solutions that comprise, for example, canine paramyxoviruses, are mixed with stabilizers and vitrified using methods according to the instant disclosure. One volume of the canine paramyxovirus suspension or solution may be mixed with one volume of the stabilizer.

Suitable preparations that may be vitrified using the disclosed methods include a canine paramyxovirus immunogenic suspension or solution and at least an active immunogenic component originating or derived from a pathogen other than paramyxoviruses. The active immunogenic component as defined herein can comprise live attenuated pathogens, such a live attenuated viruses, bacteria, fungi, or parasites. However, an active immunogenic component can also comprise killed viruses, recombinant heterologous immunogens, antigens, immunogenic subunits (e.g. proteins, polypeptides, peptides, epitopes, haptens) or epitopes of immunogens or antigens derived from or originating from one or more pathogens described herein, which can be expressed from viral vectors, bacterial vectors, plasmid vectors, and the like.

The active immunogenic component of the present invention can comprise one or more immunogens selected from a canine pathogen including, but not limited to, rabies virus, canine adenovirus type 2 (CAV2), canine herpesvirus (CHV), canine parvovirus (CPV), canine coronavirus, *Leptospira canicola*, *Leptospira icterohaemorragiae*, *Leptospira grippotyphosa*, *Borrelia burgdorferi*, *Bordetella bronchiseptica* and the like, including combinations thereof.

The active immunogenic component can include the HA, F, NP genes from the CDV, the capsid gene from CPV, the spike, M, N genes from Canine coronavirus, the HN and F genes from cPi2, genes from *Leptospira*, genes from *Bor-*

*detella*, genes from *Borrelia*, and the gB, gC and gD genes from the canine herpesvirus, among others. These components can be useful as immunogenic compositions or vaccine compositions for protecting canines against disease caused by these pathogens.

Canine Adenovirus Type 2 (CAV2) is widespread and highly contagious to dogs. It produces symptoms resembling a cold. Generally the first signs of the contagious disease are fever, which usually subsides in one to two days. Affected dogs may have tonsillitis, abdominal tenderness, enlarged liver, vomiting and diarrhea. Acute disease is normally fatal. CAV2 may be inactivated or attenuated and combined with the CDV (and/or cPi2) to produce a multivalent vaccine. Alternatively, immunogens or antigens of CAV2, or epitopes of CAV2 immunogens, such as capsid, matrix, or hexon proteins, can be used.

Canine Parvovirus (CPV) is a common intestinal virus which may cause vomiting, diarrhea, gastroenteritis, myocarditis and hepatitis in young dogs. It has been found to be widespread in dogs. CPV can be present in the immunogenic compositions, suspensions, or solutions of the invention as inactivated, live attenuated, or CPV immunogens, antigens, or epitopes of CPV immunogens, such as the VP1, VP2 (capsid) gene products.

Two common bacterial infections of dogs can also be combined in their attenuated form in the stabilized immunogenic compositions, suspensions, or solutions of the present invention; these are *Leptospira canicola* and *Leptospira icterohaemorrhagiae*. Lepto infections are common in dogs and especially in dogs infected by CDV, cPi2, or combinations of viruses as frequently observed in dogs suffering from distemper or kennel cough, and thus, their inclusions in the stabilized immunogenic compositions, suspensions, or solutions of the present invention are of significant utility.

Other active immunogenic component useful in the compositions and methods of the present invention can comprise one or more immunogens selected from avian pathogens including, but not limited to, *Salmonella typhimurium*, *Salmonella enteritidis*, Infectious Bronchitis virus (IBV), Newcastle Disease virus (NDV), egg drop syndrome virus (EDS), Infectious Bursal Disease virus (IBDV), turkey virus, avian influenza virus, Marek's disease virus, Herpesviruses such as infectious laryngotracheitis virus, avian infectious bronchitis virus, avian reovirus, poxviruses including avipox, fowlpox, canarypox, pigeonpox, quailpox, and dovepox, avian polyomavirus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, avian spleen necrosis virus, and combinations thereof.

As to specific immunogens, the active immunogenic components can also be the FIN and F genes of Newcastle Disease Virus, the polyprotein and VP2 genes from infectious Bursal Disease Virus, the S and N genes from Infectious Bronchitis Virus and the gB and gD genes from Marek's Disease Virus. These components can be used as immunogenic compositions or vaccine compositions for protecting avians against disease caused by these pathogens.

Alternatively, the active immunogenic component comprises one or more immunogens from a feline pathogen such as, but not limited to, feline herpesvirus (FHV), feline calicivirus (FCV), feline leukemia virus (FeLV), feline infectious peritonitis virus, feline panleucopenia virus, feline immunodeficiency virus (FIV), rabies virus, and the like, and combinations thereof.

The active immunogenic component can also include the gB, gC and gD genes from the Feline Herpesvirus, the env and gag/pro genes from the FeLV, the env, gag/pol and tat genes from the FIV virus, the capsid gene from the Feline calicivirus, the S modified gene, M, and N gene from the Feline Infectious Peritonitis Virus, and the VP2 gene from the Feline parvovirus. These components can be useful as immunogenic or vaccine compositions for protecting cats against disease caused by these pathogens.

The active immunogenic component can comprise one or more immunogens from an equine pathogen, such as equine herpesvirus (type 1 or type 4), equine influenza virus, equine encephalomyelitis virus (EEV), tetanus, West Nile virus, and the like or combinations thereof.

The active immunogenic component can also include, the gB, gC, gD and Immediate-Early genes from Equine herpesvirus type 1, the gB, gC, gD and Immediate-Early genes from Equine herpesvirus type 4, the HA, NA, M and NP genes from Equine influenza virus, genes from Eastern Equine Encephalitis Virus, genes from Western Equine Encephalitis Virus, genes from Venezuelan Equine Encephalitis Virus, the prM-M-E genes from the West Nile Virus, and genes from Equine arteritis virus, but are not limited to these sequences. These components can be useful as immunogenic compositions or vaccine compositions for protecting horses against disease caused by these pathogens.

The active immunogenic component can comprise one or more immunogens from a bovine pathogen, such as rabies virus, bovine rotavirus, bovine parainfluenza virus type 3 (bCPI2-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli*, *Pasteurella multocida*, *Pasteurella haemolytica*, and the like and combinations thereof.

The active immunogenic component can also be selected from the gB, gC, gD and Immediate-Early genes from Bovine Herpesvirus type 1, the F and G genes from BRSV, the polyprotein, E1, E2 genes from BVDV, the HN and F genes from PI3 virus or genes from Rotavirus. These components can be useful as immunogenic or vaccine compositions for protecting cattle against disease caused by these pathogens.

Further, the active immunogenic component can comprise one or more immunogens from a porcine pathogen such as, but not limited to, swine influenza virus (SIV), porcine circovirus type 2 (PCV-2), porcine reproductive respiratory syndrome virus (PRRSV), pseudorabies virus (PRV), porcine parvovirus (PPV), hog cholera virus (HCV), FMDV, *Mycoplasma hyopneumoniae*, *Erysipelothrix rhusiopathiae*, *Pasteurella multocida*, *Bordetella bronchiseptica*, *Escherichia coli*, and the like, and combinations thereof.

The active immunogenic component can also include the gB, gC, gD and Immediate-Early genes from PRV, the HA, NA, M and NP genes from Swine influenza virus, the polyprotein, E1, E2 from Hog Cholera Virus, the ORF1 and ORF2 genes from PCV2 virus, the ORF3, ORF4, ORF5, ORF6, or ORF7 from PRRSV virus or genes from *Mycoplasma hyopneumoniae*. These components can be useful as immunogenic compositions or vaccine compositions for protecting pigs against disease caused by these pathogens.

The active immunogenic component can comprise sequences encoding a protein expressed in pathogens such as RNA or DNA viruses like HIV, HCV, HBV, HPV, EBV, HSV, CMV, HTLV, Hanta virus, Ebola virus, Marburg virus, Rift Valley fever virus, Lassa virus and influenza virus, hemorrhagic *enteritidis* virus (HEV), infectious rhinotracheitis virus (IBRV), among others. Such immunogens can be used advantageously as immunogenic compositions or vaccine compositions to protecting subjects, such as humans, against disease caused by these pathogens.

The active immunogenic component can also be, for example, from any one of the following pathogenic bacteria and their antigens: *Actinobacillus* species such as *Actinobacillus pleuropneumoniae, Bordetella pertussis, Bordetella parapertussis, Bordetella bronchiseptica, Bordetella avium, Chlamydia trachomatis, Chlamydia pneumoniae, Chlamydia psittaci, Klebsiella* species such as *Klebsiella pneumoniae, Mycobacterium tuberculosis, Mycobacterium pseudotuberulosis, Mycobacterium pneumoniae*, Group A *Streptococcus, Streptococcus equi, Streptococcus pneumoniae, Streptococcus agalactiae, Streptococcus pyogenes, Streptococcus viridans, Neisseria gonorrhoeae, Erysipelothrix* species, *Enterotoxigenic Escherichia coli, Vibrio cholerae, Bacillus anthracis, Haemophilus influenzae, Haemophilus somnus, Haemophilus parasuis, Salmonella* species, *Salmonella agona, Salmonella blockley, Salmonella enteriditis, Salmonella hadar, Salmonella Heidelberg, Salmonella montevideo, Salmonella senftenberg, Salmonella cholerasuis, Rickettsia* species, *Helicobacter pylori, Helicobacter felis, Shigella* species, *Listeria* species, *Legionella pneumoniae, Pseudomonas* species, *Borrelia* species, *Borellia burgdorferi, Neisseria meningitides, Clostridium* species, *Clostridium difficile, Ureaplasma urealyticum, Staphylococcus* species, *Staphylococcus aureus, Enterococcus faecalis, Pasteurella pestis, Campylobacter* species, *Campylobacter jejuni, Treponema* species, *Leptospira* species, *Corynebacterium diphtheria, Hemophilus ducreyi, Hemophilus influenza, Erlichhia* species, among others.

The active immunogenic component may also be derived from a fungus or mold such as *Aspergillus flavus, Aspergillus fumigatis, Penicillium species, Fusarium species, Candida* species such as *Candida trichophyton, Candida parapsilosis, Candida glabrata, Candida dubliniensis*, and *Candida albicans, Rhizopus species, Cryptococcus* species such as *Cryptococcus neoformans, Cryptococcus grubii, Cryptococcus gattii, Paracoccidioides brasiliensis, Histoplasma capsulatum*, and other fungi and molds.

The active immunogenic component can also be selected from parasitic antigens derived from parasitic species including, but are not limited to, *Plasmodium* species, *Trypanosome* species, *Giardia* species, *Boophilus* species, *Babesia* species, *Entamoeba* species, *Eimeria* species, *Leishmania* species, *Schistosoma* species, *Brugia* species, *Fascida* species, *Dirofilaria* species, *Wuchereria* species, *Onchocerea* species, *Treponema* species, *Toxoplasma* species, *Cryptococcus* species, *Coccidia* species, *Histomoniasis* species, *Hexamitiasis* species, *Giardia* species, among others; nematodes including *Ascaris* species, *Trichinella* species, and the like, helminthes such as flukes, tapeworms, among others; and other like pathogenic organisms. Methods for preparing immunogens derived from viruses, bacteria, fungi, molds, protozoa, nematodes, and helminthes are known in the art.

Other useful immunogens can be, for example, purified secreted antigen virulence factors, such as toxins, cytotoxins, and the like. Toxin antigens which are detoxified by modifying (toxoids), which can be administered in combination with an adjuvant such as aluminum hydroxide, and can be used to stimulate the formation of toxin-neutralizing antibodies. Examples of toxins that may be used as an immunogen include bacterial endotoxins and exotoxins such as lipopolysaccharide, enterotoxins including heat-labile enterotoxins (LT), heat stable enterotoxins (ST), verotoxin (VT), and the like. Bacterial exotoxin immunogens are secreted into the surrounding medium, and include, for example, diphtheria toxin (*Corynebacterium diphtheriae*), tetanus toxin (*Clostridium tetani*), enterotoxins secreted by *Staphylococcus aureus*, botulinum toxins (*Clostridium botulinum*); and toxins produced by algae such as neurotoxins; and the like. Heat-stable endotoxins, released by autolysis of the bacteria, include, for example, cholera toxins released from the gram negative *Vibrio cholerae*, colicins produced by intestinal bacteria such as *E. coli* (bacteriocin).

Immunogens derived from, or originating from viruses, bacteria, fungi and the like may be produced by in vitro culture methods using appropriate culture medium or host cells lines and conventional methods well known to those of ordinary skill in the art. For example, PRRSV may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SIV may be cultured on eggs (U.S. Pat. No. 6,048,537); and *Mycoplasma hyopneumoniae* may be cultured in an appropriate culture medium (U.S. Pat. Nos. 5,968,525; 5,338,543; Ross R. F. et al., (1984) Am. J. Vet. Res. 45: 1899-1905). Advantageously, CDV can be cultured in mink lung cells, such as those described in U.S. Pat. No. 5,178,862. Other techniques for the preparation of virus-derived immunogens are known in the art, and described, for example, in Ulmer et al., Science 259: 1745 (1993); Male et al., Advanced Immunology, pages 14.1-14.15, J.B. Lippincott Co., Philadelphia, Pa. (1989).

Also useful are immunogenic synthetic peptides that mimic antigenic peptide sequences. Such immunogens may be synthesized using a solid-phase technique as described, for example, in R. B. Merrifield, Science 85:2149-2154 (1963), purified, and optionally coupled to a carrier protein such as muramyl dipeptide (MDP), bovine serum albumin (BSA), keyhole limpet hemocyanin (KLH), and the like, using a bifunctional coupling agent such as glutaraldehyde, and the like.

Synthetic antigens are also included within the definition, for example, polyepitopes, flanking epitopes, and other recombinant or synthetically derived antigens. See, e.g., Bergmann et al. (1993) Eur. J. Immunol. 23, 2777-2781; Bergmann et al. (1996) J. Immunol. 157, 3242-3249; Suhrbier, A. (1997) Immunol. Cell Biol. 75, 402-408; Gardner et al. (1998) 12th World AIDS Conference, Geneva, Switzerland, Jun. 28-Jul. 3, 1998. Immunogenic fragments, for purposes of the present invention, can usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length protein sequence, or even a fusion protein comprising two or more, or at least one epitope of the protein.

Accordingly, a minimum structure of a nucleic acid expressing an epitope can comprise nucleotides to encode an epitope, immunogen, or antigen of a protein or polyprotein. A nucleic acid encoding a fragment of the total protein or polyprotein, more advantageously, comprises or consists essentially of or consists of a minimum of about 21 nucleotides, advantageously at least about 42 nucleotides, and preferably at least about 57, about 87 or about 150 consecutive or contiguous nucleotides of the sequence encoding the total protein or polyprotein. Epitope determination procedures, such as, generating overlapping peptide libraries (Hemmer B. et al., (1998) Immunology Today 19(4), 163-168), Pepscan (Geysen et al. (1984) Proc. Natl. Acad. Sci. USA 81, 3998-4002; Geysen et al., (1985) Proc. Nat. Acad. Sci. USA 82, 178-182; Van der Zee R. et al., (1989) Eur. J. Immunol. 19, 43-47; Geysen H. M., (1990) Southeast Asian J. Trop. Med. Public Health 21, 523-533; MULTIPIN® Peptide Synthesis Kits from Chiron) and algorithms (De Groot A. et al., (1999) Nat. Biotechnol. 17, 533-561), and in PCT Application Serial No. PCT/US2004/022605; all of which are incorporated herein by reference in their entireties can be used in the practice of the invention, without undue experimentation. Other documents cited and incorporated herein may also be consulted for methods for determining epitopes of an immunogen or antigen and thus nucleic acid molecules that encode such epitopes.

In the present invention, the active immunogenic component can also comprise an a therapeutic agent, a cytokine, a toxin, an immunomodulator, a protein, a peptide, an antibody, an antigen-binding fragment of an antibody, an adjuvant, or any other molecule encodable by DNA and desired for delivery to an animal or animal cell or tissue.

Also contemplated by the present invention are the inclusion of antisense, catalytic, or small interfering RNA species in the immunogenic compositions and vaccine compositions of the present invention, which can be targeted against any molecule present within the recipient cell or likely to be present within the recipient cell. These include, but are not limited to RNA species encoding cell regulatory molecules, such as interleukin-6, causative agents of cancer such as human papillomavirus, enzymes, viral RNA and pathogen-derived RNA, such as HIV-1 RNA. The RNAs can also be targeted at non-transcribed DNA sequences, such as promoter or enhancer regions, or to any other molecule present in recipient cells, such as but not limited to, enzymes involved in DNA synthesis or tRNA molecules.

In addition, cytokines and immunomodulators can be co-expressed in the immunogenic compositions and vaccine compositions of the present invention. Examples include, but are not limited to, IL-2, IL-4, TNF-α, GM-CSF, IL-10, IL-12, IGF-1, IFN-α, IFN-β, and IFN-γ.

Specific sequence motifs, such as the RGD motif, may be inserted into the H-I loop of a viral or plasmid vector to enhance its infectivity. This sequence has been shown to be essential for the interaction of certain extracellular matrix and adhesion proteins with a superfamily of cell-surface receptors called integrins. Insertion of the RGD motif may be advantageously useful in immunocompromised subjects. A recombinant vector can be constructed by cloning specific antigen or immunogen or fragments thereof into any of the vectors such as those described herein. The recombinant vector can be used to transduce cells of a vertebrate for use as an immunizing agent. (See, for example, U.S. patent application Ser. No. 10/424,409, incorporated by reference).

Preferably, codons encoding active immunogenic components, such as antigens, immunogens and epitopes, are "optimized" codons, i.e., the codons are those that appear frequently in, i.e., highly expressed canine genes, instead of those codons that are frequently used by, for example, CDV or cPi2. Such codon usage provides for efficient expression of the active immunogenic component in cells. In other embodiments, for example, when the active immunogenic component is expressed in bacteria, yeast or other expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al, 1998; McEwan et al. 1998).

In some cases it may be necessary to modify the coding sequence so that it may be attached to the control sequences with the appropriate orientation; i.e., to maintain the proper reading frame. It may also be desirable to produce mutants or analogs of the desired active immunogenic components. Mutants or analogs may be prepared by the deletion of a portion of a sequence encoding a protein, by insertion of a sequence, and/or by substitution of one or more nucleotides within a sequence. Techniques for modifying nucleotide sequences, such as site-directed mutagenesis, are described in, e.g., Sambrook et al., supra; DNA Cloning, supra; Nucleic Acid Hybridization, supra.

Immunogens useful as active immunogenic components according to the present invention can be contained vectors. Such vectors include, but are not limited to, in vivo recombinant expression vectors such as a nucleic acid vector or a plasmid (EP Application No. 1001025; Chaudhuri P, (2001) Res. Vet. Sci. 70, 255-6), virus vectors such as, but not limited to, adenovirus vectors, poxvirus vectors such as fowlpox (U.S. Pat. Nos. 5,174,993; 5,505,941; and 5,766,599) canarypox vectors (U.S. Pat. No. 5,756,103), retroviral vectors, herpes virus vectors, vectors based on alphavirus, fungal vectors, or bacterial vectors (*Escherichia coli* or *Salmonella* species). Specific examples of vectors useful in the invention are described herein.

The vector can be a viral vector, advantageously an avipox vector containing at least one active immunogenic component, or an epitope thereof, or a fragment thereof. In a particularly advantageous embodiment, the avipox vector is a canarypox vector, advantageously, an attenuated canarypox vector such as ALVAC®. Attenuated canarypox viruses are described in U.S. Pat. No. 5,756,103 (ALVAC®) and WO01/05934. The avipox vector can be a fowlpox vector, advantageously an attenuated fowlpox vector such as TROVAC®. Reference is also made to U.S. Pat. No. 5,766,599 that pertains to the attenuated fowlpox strain TROVAC®. In this regard, reference is made to the canarypox available from the ATCC under access number VR-111. Numerous fowlpox virus immunization strains are also available, e.g. the DIFTOSEC CT™ strain marketed by Merial and the NOBILIS VARIOLE™ vaccine marketed by Intervet; and, reference is also made to U.S. Pat. No. 5,766,599 which pertains to the attenuated fowlpox strain TROVAC®.

A viral vector also useful to deliver active immunogenic components include a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, (1971) Munch. Med. Wschr. 113, 1149-1153; Sutter et al. (1992) Proc. Natl. Acad. Sci. U.S.A. 89, 10847-10851; available as ATCC VR-1508; or NYVAC®, see U.S. Pat. No. 5,494,807, for instance, Examples 1 to 6 of U.S. Pat. No. 5,494,807 which discuss the construction of NYVAC®, as well as variations of NYVAC® with additional ORFs deleted from the Copenhagen strain vaccinia virus genome, as well as the insertion of heterologous nucleic acid coding sequences into sites of this recombinant, and also, the use of matched promoters; see also WO96/40241), an avipox virus or an attenuated avipox virus (e.g., canarypox, fowlpox, dovepox, cowpox, pigeonpox, quailpox, ALVAC® or TROVAC®; see, e.g., U.S. Pat. Nos. 5,505,941, 5,494,807), swinepox, raccoonpox, camelpox, or myxomatosis virus.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030, inter alia.

When the expression vector is a vaccinia virus, insertion site or sites for the nucleic acid or nucleic acids encoding active immunogenic components such as immunogens, antigens, epitopes and the like, to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al. (1997) Vaccine 15(4), 387-394; Stittelaar K. J. et al. (2000) J. Virol., 2000, 74(9), 4236-4243; Sutter G. et al. (1994) Vaccine 12(11), 1032-1040; and, in this regard it is also noted that the complete MVA genome is described in Antoine G., (1998) Virology 244, 365-396, which enables the skilled artisan to use other insertion sites or other promoters.

Advantageously, the nucleic acid to be expressed can be inserted under the control of a specific poxvirus promoter, e.g., the vaccinia promoter 7.5 kDa (Cochran et al., (1985) J. Virology 54, 30-35), the vaccinia promoter I3L (Riviere et al., (1992) J. Virology 66, 3424-3434), the vaccinia promoter HA (Shida, (1986) Virology 150, 451-457), the vaccinia promoter 42K (Cooper J. A. et al, (1981) J. Virol. 37(1), 284-94), the cowpox promoter ATI (Funahashi et al (1988) J. Gen. Virol. 69, 35-47), the vaccinia 11K promoter (U.S. Pat. No. 5,017,487); the vaccinia promoter H6 (Taylor J. et al., (1988) Vaccine 6, 504-508; Guo P. et al. (1989) J. Virol. 63, 4189-4198; Perkus M. et al. (1989) J. Virol. 63, 3829-3836), or synthetic vaccinia or poxviral promoters, inter alia.

Advantageously, for the immunization of mammals, the expression vector can be a canarypox or a fowlpox vector. In this way, there can be expression of the heterologous proteins with limited or no productive replication.

Another viral vector useful to deliver and express active immunogenic components is adenovirus. Adenovirus is a non-enveloped DNA virus. Vectors derived from adenoviruses have a number of features that make them particularly useful for gene transfer. A recombinant adenovirus vector is an adenovirus vector that carries one or more heterologous nucleotide sequences (e.g., two, three, four, five or more heterologous nucleotide sequences). For example, the biology of the adenoviruses is characterized in detail, the virus is extremely efficient in introducing its DNA into the host cell, the virus can infect a wide variety of cells and has a broad host range, the virus can be produced in large quantities with relative ease, and the virus can be rendered replication defective by deletions in the early region 1 ("E1") of the viral genome.

In contrast to, for example, retroviruses, adenoviruses do not integrate into the host cell's genome, are able to infect non-dividing cells, and are able to efficiently transfer recombinant genes in vivo (Brody et al., 1994). These features make adenoviruses attractive candidates for in vivo gene transfer of, for example, a heterologous nucleic acid of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective adenovirus. As long as one of the deletions renders the adenovirus replication defective, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective. More preferably, all of the deletions are deletions that would render the adenovirus replication defective.

Embodiments of the invention employing adenovirus recombinants may include E1-defective or deleted, E3-defective or deleted, and/or E4-defective or deleted adenovirus vectors, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-immunization utilizing the same vector. The present invention comprehends adenovirus vectors of any serotype or serogroup that are deleted or mutated in E1, E3, E4, E1 and E3, and E1 and E4.

A "gutless" adenovirus vector is the latest model in the adenovirus vector family and is derived from human adenovirus sequences. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated multiple times for reimmunization. The "gutless" adenovirus vector also contains 36 kb space for accommodating heterologous nucleic acid(s) of interest, thus allowing co-delivery of a large number of antigen or immunogens into cells.

Thus, the vector in the invention can be any suitable recombinant virus or virus vector, including, without limitation, a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, (as in documents incorporated herein by reference); or the vector can be a plasmid. The herein cited and incorporated herein by reference documents, in addition to providing examples of vectors useful in the practice of the invention, can also provide sources for other active immunogenic components to be expressed by vector or vectors in, or included in, the stabilized immunogenic compositions, suspensions, or solutions of the invention.

Elements for the expression of the active immunogenic components can advantageously be present in a plasmid vector. The term plasmid covers any DNA transcription unit comprising a nucleic acid according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

In a minimum manner, expression of an active immunogenic component, such as an antigen, an immunogen, and an epitope, comprises an initiation codon (ATG), a stop codon and a promoter, and optionally also a polyadenylation sequence for certain vectors such as plasmid and certain viral vectors, e.g., viral vectors other than poxviruses. When the nucleic acid encodes a polyprotein fragment in the vector, an ATG is placed at the 5' terminus of the reading frame and a stop codon is placed at the 3' terminus. Other elements for controlling expression may be present, such as enhancer sequences, stabilizing sequences and signal sequences permitting the expression, modification, and secretion of the protein.

A nucleic acid "coding sequence" or a "nucleotide sequence encoding" a particular protein is a DNA sequence which is transcribed and translated into a polypeptide in vitro or in vivo when placed under the control of appropriate regulatory elements. The boundaries of the coding sequence are determined by a start codon at the 5' terminus and a translation stop codon at the 3' terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

Nucleic acid "control elements" refer collectively to promoters, RNA splice sites, ribosome binding sites, polyadenylation signals (e.g., polyadenylation signals derived from bovine growth hormone, SV40 polyadenylation signal), transcription termination sequences, upstream regulatory domains, enhancers, origins of replication (which can be bacterial origins, e.g., derived from bacterial vectors such as pBR322, or eukaryotic origins, e.g., autonomously replicating sequences (ARS)), packaging signals, leader sequences that may or may not be contained in the coding sequence of an active immunogenic component, such as an immunogen, antigen or epitope. If a signal sequence is included, it can either be the native, homologous sequence, or a heterologous sequence. Leader sequences can be removed by the host in post-translational processing. See, e.g., U.S. Pat. Nos. 4,431,739; 4,425,437; 4,338,397, and the like, which collectively provide for the transcription and translation of a coding sequence in a host cell.

Not all of these control sequences need always be present in a recombinant vector so long as the desired gene is capable of being transcribed and translated. A control element, such as a promoter "directs the transcription" of a coding sequence in a cell when RNA polymerase binds to the promoter and transcribes the coding sequence into mRNA. The resultant mRNA is subsequently translated into the polypeptide encoded by the coding sequence.

A variety of promoter/enhancer elements may be used depending on the level and tissue-specific expression desired. The promoter can be constitutive or inducible (e.g., the metallothionein promoter, the tetracycline inducible promoter, and the ecdysone inducible promoter, among others), depending on the pattern of expression desired. The promoter may be native or heterologous and can be a natural or a synthetic sequence. "Heterologous" in this context describes a transcriptional initiation region that is not found in the wild-type host into which the transcriptional initiation region is introduced. The promoter is chosen so that it will function in the target cell(s) or tissue(s) of interest. Brain-specific, hepatic-specific, and muscle-specific (including skeletal, cardiac, smooth, and/or diaphragm-specific) promoters are contemplated by the present invention. Mammalian and avian promoters are also preferred, particularly canine promoters.

The promoter can advantageously be an "early" promoter. An "early" promoter is known in the art and is defined as a promoter that drives expression of a gene that is rapidly and transiently expressed in the absence of de novo protein synthesis. The promoter can also be a "strong" or "weak" promoter. The terms "strong promoter" and "weak promoter" are known in the art and can be defined by the relative frequency of transcription initiation (times per minute) at the promoter. A "strong" or "weak" promoter can also be defined by its affinity to RNA polymerase.

The heterologous gene can be placed under the control of a promoter, ribosome binding site (for bacterial expression) and, optionally, an enhancer or operator, so that the DNA sequence encoding the desired protein is transcribed into RNA in a host cell or subject transformed by a vector containing the active immunogenic component.

Control elements and other regulatory sequences may be ligated to the coding sequence prior to insertion into a vector, such as the cloning vectors described above. Alternatively, the coding sequence can be cloned directly into an expression vector that already contains the control sequences and an appropriate restriction site.

More preferably, the antigens or immunogens are operatively associated with, for example, a human cytomegalovirus (CMV) major immediate-early promoter, a simian virus 40 (SV40) promoter, a β-actin promoter, an albumin promoter, an Elongation Factor 1-α (EF1-α) promoter, a PγK promoter, a MFG promoter, or a Rous sarcoma virus promoter. Other expression control sequences include promoters derived from immunoglobin genes, adenovirus, bovine papilloma virus, herpes virus, and so forth. Any mammalian viral promoter can also be used in the practice of the invention, in addition to any canine viral promoter. Among canine promoters of viral origin, the promoters of immediate early genes of the infectious canine herpes virus, early (i.e., thymidine kinase, DNA helicase, ribonucleotide reductase) or late promoters, can be used in the methods and vectors of the present invention. Other promoters include the E1 promoter of canine adenovirus, as well as the canine major histocompatibility complex I promoter. Moreover, it is well within the purview of the skilled artisan to select a suitable promoter that expresses the antigen or immunogen of interest at sufficiently high levels so as to induce or elicit an immunogenic response to the antigen or immunogen, without undue experimentation.

It has been speculated that driving heterologous nucleotide transcription with the CMV promoter can result in downregulation of expression in immunocompetent animals (see, e.g., Guo et al., 1996). Accordingly, it is also preferred to operably associate the antigen or immunogen sequences with, for example, a modified CMV promoter that does not result in this downregulation of antigen or immunogen expression.

The vectors of the invention can also comprise a polylinker or multiple cloning site ("MCS"), which can advantageously be located downstream of a promoter. The polylinker provides a site for insertion of the antigen or immunogen molecules that are "in-frame" with the promoter sequence, resulting in "operably linking" the promoter sequence to the antigen or immunogen of interest. Multiple cloning sites and polylinkers are well known to those skilled in the art.

The vectors described herein can also comprise antibiotic resistance genes. Examples of such antibiotic resistance genes that can be incorporated into the vectors of the invention include, but are not limited to, ampicillin, tetracycline, neomycin, zeocin, kanamycin, bleomycin, hygromycin, chloramphenicol, among others.

In embodiments where there is more than one antigen or immunogen, the antigen or immunogen sequences may be operatively associated with a single upstream promoter and one or more downstream internal ribosome entry site (IRES) sequences (e.g., the picornavirus EMC IRES sequence). An IRES sequence allows for multicistronic translation of two or more coding sequences from a single mRNA sequence.

The vectors of the invention can then be used to transform an appropriate host cell or subject. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, Madin-Darby canine kidney ("MDCK") cells, as well as others. Similarly, bacterial hosts such as *E. coli, Bacillus subtilis, Salmonella* spp., *Shigella* spp., and *Streptococcus* spp., will find use in the present invention. Yeast hosts useful in the present invention include inter alia, *Saccharomyces cerevisiae, Candida albicans, Candida maltosa, Hansenula polymorphs, Kluyveromyces fragilis, Kluyveromyces lactis, Pichia guillerimondii, Pichia pastoris, Schizosaccharomyces pombe* and *Yarrowia lipolytica.* Insect hosts useful in the present invention include, but are not limited to, *Spodoptera frugiperda* cells.

Alternatively, the vectors can be used to infect a cell in culture to express a desired gene product, e.g., to produce a protein or peptide of interest. Preferably, the protein or peptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. Preferably, the cell is a vertebrate cell, more preferably a mammalian cell.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; W091/11525; WO 94/16716; WO 96/39491; WO 98/33510; EP 265785; EP 0 370 573; Andreansky et al. (1996) Proc. Natl. Acad. Sci. USA 93, 11313-11318; Ballay et al. (1993) EMBO J. 4, 3861-65; Felgner et al. (1994) J. Biol. Chem. 269, 2550-2561; Frolov et al. (1996) Proc. Natl. Acad. Sci. USA 93, 11371-11377; Graham, F. L. (1990) Trends Biotechnol. 8, 85-87; Grunhaus et al. (1992) Sem. Virol. 3, 237-52; Ju et al. (1998) Diabetologia 41, 736-739; Kitson et al. (1991) J. Virol. 65, 3068-3075; McClements et al. (1996) Proc. Natl. Acad. Sci. USA 93, 11414-11420; Moss, B. (1996) Proc. Natl. Acad. Sci. USA 93, 11341-11348; Paoletti, E. (1996) Proc. Natl. Acad. Sci. USA 93, 11349-11353; Pennock et al. (1984) Mol. Cell. Biol. 4, 399-406; Richardson (Ed), (1995) Methods in Molecular Biology 39, "Baculovirus Expression Protocols," Humana Press Inc.; Smith et al. (1983) Mol. Cell. Biol. 3, 2156-2165; Robertson et al. (1996) Proc. Natl. Acad. Sci. USA 93, 11334-11340; Robinson et al. (1997) Sem. Immunol. 9, 271; and Roizman, B. (1996) Proc. Natl. Acad. Sci. USA 93, 11307-11312.

Expression in the subject of the heterologous sequence can result in an immune response in the subject to the expression products of the antigen or immunogen. Thus, the active immunogenic components of the present invention may be used in an immunogenic composition or vaccine composition to provide a means to induce an immune response, which may, but need not be, protective. The molecular biology techniques used in the context of the invention are described by Sambrook et al. (2001).

Even further alternatively or additionally, in the immunogenic or vaccine compositions encompassed by the present invention, the nucleotide sequence encoding the antigens or immunogens can have deleted therefrom a portion encoding a transmembrane domain. Yet even further alternatively or additionally, the vector or immunogenic composition can further contain and express in a host cell a nucleotide sequence encoding a heterologous tPA signal sequence such as a mammalian tPA and/or a stabilizing intron, such as intron II of the rabbit β-globin gene.

A vector can be administered to a subject in an amount to achieve the amounts stated for gene product (e.g., epitope, antigen, therapeutic, and/or antibody) compositions. The invention envisages dosages below and above those exemplified herein, and for any composition to be administered to a subject, including the components thereof, and for any particular method of administration, it is preferred to determine toxicity, such as by determining the median cell culture infective dose ($CCID_{50}$), the lethal dose (LD) and $LD_{50}$ in a suitable subject; and the dosage of the composition, concentration of components therein and timing of administering the composition, which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein.

Multivalent immunogenic compositions and/or vaccine compositions and/or immunogenic suspensions or solutions comprising live attenuated CAV2, live attenuated CDV, live attenuated cPi2, and live attenuated CPV, and comprising a stabilizer according to the present invention have been tested in the Examples herein. These multivalent vaccines showed good stability for CDV, cPi2, CAV2 and CPV. This demonstrates that the stabilizers of the present invention are able to preserve viability and infectivity of CDV, cPi2, CAV2 and CPV. This also demonstrates that the stabilizers of the present invention are able to preserve viability and infectivity of a variety of viruses other than canine paramyxoviruses, notably of canine parvovirus and canine adenovirus. The stabilizers according to the present invention can be also used as a monovalent immunogenic composition or vaccine composition comprising CAV, CPV, CDV or cPi2.

The cooling step (b) can occur at temperatures of less than about −40° C. (water freezing step). Drying the stabilized immunogenic suspensions or solution by sublimation of ice at low pressure (c) can occur at, for example, pressure lower than or equal to about 200 μbar, whereas a further reduction in pressure can occur at pressures lower than or equal to about 100 μbar. Finally, the temperature of the stabilized immunogenic suspension or solution during the removal of excess residual water (d) occurs at, for example, temperatures between about 20° C. and about 30° C.

The process of freeze-drying can also be performed with an immunogenic suspension or solution comprising live attenuated canine paramyxovirus and at least one active immunogenic component derived from a pathogen other than a paramyxovirus, which is mixed with a stabilizer according to the invention to obtain a freeze-dried stabilized multivalent immunogenic or vaccine composition.

The moisture content of the vitrified material can range from about 0.5% to about 5% w/w, preferably from about 0.5% to about 3% w/w, and more preferably from about 1.0% to about 2.6% w/w.

For its use and administration into a subject, the vitrified stabilized immunogenic composition or vaccine composition can be reconstituted by rehydration with a solvent. The solvent is typically water, such as demineralized or distilled water, water-for-injection, but can also comprise physiological solutions or buffers, such as for example phosphate buffer solution (PBS), or adjuvants including, but not limited to, water-in-oil emulsions, *Corynebacterium parvum*, *Bacillus* Calmette Guerin, aluminum hydroxide, glucan, dextran sulfate, iron oxide, sodium alginate, Bacto-Adjuvant, certain synthetic polymers such as poly amino acids and copolymers of amino acids, saponin, "REGRESSIN®" (Vetrepharm, Athens, Ga.), "AVRIDINE®" (N, N-dioctadecyl-N', N'-bis(2-hydroxyethyl)-propanediamine), paraffin oil, muramyl dipeptide and the like. Other specific examples of adjuvants and adjuvant compositions are detailed herein.

Suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference), which discusses such acrylic polymers cross-linked with a polyhydroxylated compound containing at least 3 hydroxyl groups; a polyhydroxylated compound contains not more than 8 hydroxyl groups; as another example, the hydrogen atoms of at least 3 hydroxyls are replaced with unsaturated aliphatic radicals containing at least 2 carbon atoms. Radicals can contain from about 2 to about 4 carbon atoms, e.g., vinyls, allyls and other ethylenically unsaturated groups. The unsaturated radicals can themselves contain other substituents, such as methyl. The products sold under the name CARBOPOL® (Noveon Inc., Ohio, USA) are particularly suitable for use as adjuvants. They are cross-linked with an allyl sucrose or with allyl-pentaerythritol, as to which, mention is made of the products CARBOPOL® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example, cross-linked with divinyl ether. Also, reference may be made to U.S. Pat. No. 6,713,068 and Regelson, W. et al., 1960; (incorporated by reference).

Cationic lipids containing a quaternary ammonium salt are described in U.S. Pat. No. 6,713,068, the contents of which are incorporated by reference, can also be used in the methods and compositions of the present invention. Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidylethanolamine; Behr J. P. et al, 1994), to form DMRIE-DOPE.

The total content of components in reconstituted ready-to-inject immunogenic compositions or vaccine compositions of the invention can be used to provide an injection at an isotonic concentration, e.g., within the range of about 100-600 mOsm, generally within about 250-450 mOsm, and preferably about 330 mOsm.

Dosages of live attenuated pathogens, notably CDV and cPi2, in a freeze-dried stabilized immunogenic compositions or vaccine composition, or in reconstituted ready-to-inject immunogenic compositions or vaccine compositions, can range from about $10^2$ to about $10^7$ $CCID_{50}$/dose. For proteins, polypeptides or glycoproteins in a freeze-dried stabilized multivalent immunogenic composition or vaccine composition, or in the reconstituted ready-to-use multivalent immunogenic compositions or vaccine compositions, can range in an equivalent titer before inactivation from about $10^5$ to about $10^9$ $CCID_{50}$ per dose, preferably from about $10^6$ to about $10^8$ $CCID_{50}$ per dose.

The reconstituted ready-to-use immunogenic compositions or vaccine compositions can be administered to an animal by injection through the parenteral or mucosal route, preferably intramuscular and subcutaneous. However, administration of such reconstituted ready-to-use immunogenic compositions or vaccine compositions can also comprise intranasal, epicutaneous, topical, or oral administration. The volume of a dose for injection can be from about 0.1 ml to about 2.0 ml, and preferably about 1.0 ml.

The invention will now be further described by way of the following non-limiting Examples, given by way of illustration of various embodiments of the invention and are not meant to limit the present invention in any fashion.

EXAMPLES

Example 1: Vitrification Process—Biological Material (General Followed by Specific)

The biological compositions were vitrified according to the following general steps:

(1) formulating a biologic preparation, including the steps of adding active biologic ingredients, adding stabilizers, which reduce or eliminate damage induced by subjecting biologic ingredients to cryogenic preservation means, including prilling, vitrification, and freeze-drying, and optionally adding one or more adjuvants, which increase the immunogenicity of the biologic in the case of immunological preparations;

(2) filling vials with the biologic preparation of step (1);

(3) loading of vials into temperature-controlled container, wherein the temperature is between −15° C. and 10° C., particularly between −10° C. and 5° C., and even more particularly about 5° C.;

(4) reducing the air pressure of the temperature-controlled container until a pressure within the range of 15-30 mbars is obtained;

(5) maintaining the pressure obtained during step (4) for between 5 and 20 minutes, particularly between 10 and 15 minutes, to allow the temperature of the product to stabilize and to allow volatile gases, including carbonates, to be released from the biologic preparation, wherein the container temperature remains at about 4° C. to about 6° C., or about 5° C. during this step;

(6) decreasing the container air pressure to about 4 to about 7 mbars, or about 5 mbars, for between about 5 to about 20 minutes;

(7) maintaining the pressure of step (6) for about 30 to about 60 minutes, which allows the biologic preparation to become more concentrated;

(8) increasing the temperature of the container from negative to positive temperature (between about 30° C. to about 50° C.) over the course of between 45 and 85 minutes, or about 60 minutes, and holding the pressure constant until reaching about 10° C. to about 20° C., or about 15° C.;

(9) reducing container air pressure to about 1.5 to about 4 mbars, or about 3 mbars, to accelerate the concentration, and until the container temperature reaches and maintains about 30° C. for about 30 minutes to about 90 minutes, or 60 minutes;

(10) further reducing pressure to between about 0.5 and about 4.0 mbars, or about 1 mbar, and maintaining constant pressure until foaming has completed;

(11) further reducing pressure to between about 5 μbar and about 100 μbar, or about 25 μbar, while maintaining the temperature at about 30° C. for about 400 to about 2400 or more minutes, until the desired moisture of between about 0.5% to about 15%, or about 1% to about 4%, is obtained;

(12) stoppering the vials while in the freeze-dryer container, thereby completing the vitrification method.

TABLE 2

Vitrification of RECOMBITEK ® (EURICAN, Merial) Canine Distemper Virus (CDV) & Parainfluenza Type 2 (PI2); HR 4%

| | Pressure | | Dryer | | | | |
|---|---|---|---|---|---|---|---|
| | | | Shelf Temperature | | | Trap Temperature | |
| step | Tps Min | Pressure mbar | step | Tps Min | Temp °c. | step | Tps Min | Temp °c. |
| decreasing vacuum | 0 | 238 | refrig. plates | 0 | −10 | refrig. trap | 20 | −70 |
| decreasing vacuum | 10 | 30 | heating plate | 20 | −4 | | | |
| stable vacuum | 20 | 30 | stable | 35 | −4 | | | |
| decreasing vacuum | 10 | 5 | heating plate | 60 | 30 | | | |
| stable vacuum | 40 | 5 | stable | 1275 | 30 | | | |
| decreasing vacuum | 10 | 3 | | | | | | |
| stable vacuum | 15 | 3 | | | | | | |
| decreasing vacuum | 5 | 1.5 | | | | | | |
| stable vacuum | 160 | 1.5-1 | | | | | | |
| high vacuum | 1050 | / | | | | | | |

TABLE 3

Vitrification of IB88: HR 3.9%

| | Pressure | | Dryer | | | | |
|---|---|---|---|---|---|---|---|
| | | | Shelf Temperature | | | Trap Temperature | |
| step | Tps Min | Pressure mbar | step | Tps Min | Temp °c. | step | Tps Min | Temp °c. |
| decreasing vacuum | 0 | 247 | refrig. plates | 0 | −7 | refrig. trap | 20 | −70 |
| decreasing vacuum | 10 | 20 | heating plate | 25 | −4 | | | |
| stable vacuum | 15 | 20 | stable | 20 | −4 | | | |
| decreasing vacuum | 5 | 5 | heating plate | 60 | 30 | | | |
| stable vacuum | 50 | 5 | stable | 1375 | 30 | | | |
| decreasing vacuum | 10 | 3 | | | | | | |
| stable vacuum | 30 | 3 | | | | | | |
| decreasing vacuum | 5 | 2 | | | | | | |
| stable vacuum | 85 | 2-1.5 | | | | | | |
| high vacuum | 1270 | / | | | | | | |

TABLE 4

CEP-parquet MO23 cells; EB66 cells; Vitrification of CEP 50/50 S32 + S 325 g/L; Vitrification of EB66 50/50 S32 + S 325 g/L

| | Pressure | | Dryer | | | | |
|---|---|---|---|---|---|---|---|
| | | | Shelf Temperature | | | Trap Temperature | |
| step | Tps Min | Pressure mbar | step | Tps Min | Temp °c. | step | Tps Min | Temp °c. |
| decreasing vacuum | 0 | 780 | refrig. plates | 0 | −11 | refrig. trap | 30 | −70 |
| decreasing vacuum | 10 | 22 | heating plate | 5 | −5 | | | |
| stable vacuum | 10 | 22 | stable | 40 | −5 | | | |
| decreasing vacuum | 5 | 5 | heating plate | 70 | 30 | | | |
| stable vacuum | 50 | 5 | stable | 1335 | 30 | | | |
| decreasing vacuum | 5 | 3 | | | | | | |
| stable vacuum | 40 | 3 | | | | | | |
| decreasing vacuum | 10 | 2 | | | | | | |
| stable vacuum | 5 | 2 | | | | | | |
| decreasing vacuum | 10 | 1.5 | | | | | | |
| stable vacuum | 10 | 1.5 | | | | | | |
| decreasing vacuum | 10 | 1 | | | | | | |
| stable vacuum | 125 | 1 | | | | | | |
| high vacuum | 1150 | / | | | | | | |

TABLE 5

CEP-parquet 09/17 cells; Vitrification of CEP 50/50 S32 + S 325 g/L

| step | Pressure Tps Min | Pressure sure mbar | Dryer Shelf Temperature step | Dryer Shelf Temperature Tps Min | Dryer Shelf Temperature Temp °c. | Trap Temperature step | Trap Temperature Tps Min | Trap Temperature Temp °c. |
|---|---|---|---|---|---|---|---|---|
| decreasing vacuum | 0 | 660 | refrig. plates | 0 | −5 | refrig. trap | 30 | −70 |
| decreasing vacuum | 10 | 15 | stable | 45 | −5 | | | |
| stable vacuum | 10 | 15 | heating plate | 60 | 30 | | | |
| decreasing vacuum | 10 | 5 | stable | 1330 | 30 | | | |
| stable vacuum | 50 | 5 | | | | | | |
| decreasing vacuum | 10 | 3 | | | | | | |
| stable vacuum | 20 | 3 | | | | | | |
| decreasing vacuum | 10 | 2.5 | | | | | | |
| decreasing vacuum | 10 | 2 | | | | | | |
| decreasing vacuum | 10 | 1.5 | | | | | | |
| stable vacuum | 20 | 1.5 | | | | | | |
| high vacuum | 1275 | / | | | | | | |

TABLE 6

Vitrification of MAREK: HR 5.4%

| step | Pressure Tps Min | Pressure sure mbar | Dryer Shelf Temperature step | Dryer Shelf Temperature Tps Min | Dryer Shelf Temperature Temp °c. | Trap Temperature step | Trap Temperature Tps Min | Trap Temperature Temp °c. |
|---|---|---|---|---|---|---|---|---|
| decreasing vacuum | 0 | 780 | refrig. plates | 0 | −5 | refrig. trap | 20 | −70 |
| decreasing vacuum | 10 | 23 | stable | 45 | −5 | | | |
| stable vacuum | 10 | 20 | heating plate | 65 | 30 | | | |
| decreasing vacuum | 10 | 5 | stable | 1325 | 30 | | | |
| stable vacuum | 50 | 5 | | | | | | |
| decreasing vacuum | 10 | 3 | | | | | | |
| stable vacuum | 10 | 3 | | | | | | |
| decreasing vacuum | 10 | 2 | | | | | | |
| stable vacuum | 10 | 2 | | | | | | |
| decreasing vacuum | 10 | 1.5-1 | | | | | | |
| stable vacuum | 50 | 1.5-1 | | | | | | |
| high vacuum | 1255 | / | | | | | | |

TABLE 7

Vitrification of vCP97 50/50 S11 + S 325 g/L: HR 8.42%;
Vitrification of vCP2017 50/50 S11 + S 325 g/L: HR 7.61%;
Vitrification of vCP97 50/50 F2 + S 325 g/L: HR 8.76%;
Vitrification of vCP2017 50/50 F2 + S 325 g/L: HR 7.06%

| step | Pressure Tps Min | Pressure sure mbar | Dryer Shelf Temperature step | Dryer Shelf Temperature Tps Min | Dryer Shelf Temperature Temp °c. | Trap Temperature step | Trap Temperature Tps Min | Trap Temperature Temp °c. |
|---|---|---|---|---|---|---|---|---|
| decreasing vacuum | 0 | 122 | refrig. plates | 0 | −10 | refrig. trap | 30 | −70 |
| decreasing vacuum | 10 | 23 | heating plate | 10 | −5 | | | |
| stable vacuum | 20 | 23 | stable | 20 | −5 | | | |
| decreasing vacuum | 15 | 5 | heating plate | 100 | 30 | | | |
| stable vacuum | 45 | 5 | stable | 1325 | 30 | | | |
| decreasing vacuum | 10 | 3 | | | | | | |
| stable vacuum | 10 | 3 | | | | | | |
| decreasing vacuum | 5 | 2 | | | | | | |
| stable vacuum | 5 | 2 | | | | | | |
| decreasing vacuum | 10 | 1.5 | | | | | | |
| decreasing vacuum | 10 | 1 | | | | | | |
| stable vacuum | 10 | 1 | | | | | | |
| high vacuum | 1295 | / | | | | | | |

TABLE 8

Vitrification of vCP97 50/50 S11 + S 325 g/L: HR 13.1%;
Vitrification of vCP97 50/50 F2 + S 325g/L :: HR 8.2%

| step | Pressure Tps Min | Pressure sure mbar | Dryer Shelf Temperature step | Dryer Shelf Temperature Tps Min | Dryer Shelf Temperature Temp °c. | Trap Temperature step | Trap Temperature Tps Min | Trap Temperature Temp °c. |
|---|---|---|---|---|---|---|---|---|
| decreasing vacuum | 0 | 412 | refrig. plates | 0 | 4 | refrig. trap | 30 | −70 |
| decreasing vacuum | 5 | 17 | stable | 20 | 4 | | | |
| stable vacuum | 10 | 17 | heating plate | 70 | 30 | | | |
| decreasing vacuum | 5 | 14 | stable | 1620 | 30 | | | |
| stable vacuum | 10 | 14 | | | | | | |
| decreasing vacuum | 5 | 12 | | | | | | |
| decreasing vacuum | 5 | 10 | | | | | | |
| decreasing vacuum | 10 | 8 | | | | | | |
| stable vacuum | 10 | 8 | | | | | | |
| decreasing vacuum | 5 | 6 | | | | | | |
| stable vacuum | 10 | 6 | | | | | | |
| decreasing vacuum | 5 | 4 | | | | | | |
| stable vacuum | 5 | 4 | | | | | | |

TABLE 8-continued

Vitrification of vCP97 50/50 S11 + S 325 g/L: HR 13.1%;
Vitrification of vCP97 50/50 F2 + S 325g/L :: HR 8.2%

| | Pressure | | Dryer | | | |
|---|---|---|---|---|---|---|
| | | | Shelf Temperature | | Trap Temperature | |
| step | Tps Min | Pressure mbar | step | Tps Min | Temp °c. | step Tps Min Temp °c. |
| decreasing vacuum | 5 | 2 | | | | |
| decreasing vacuum | 5 | 1.3 | | | | |
| stable vacuum | 60 | 1.3 | | | | |
| high vacuum | 1570 | / | | | | |

TABLE 9

Vitrification of PA Newcastle: HR 4.6%

| | Pressure | | Dryer | | | | |
|---|---|---|---|---|---|---|---|
| | | | Shelf Temperature | | Trap Temperature | | |
| step | Tps Min | Pressure mbar | step | Tps Min | Temp °c. | step | Tps Min | Temp °c. |
| decreasing vacuum | 0 | 520 | refrig. plates | 0 | 4 | refrig. trap | 20 | -70 |
| decreasing vacuum | 5 | 22 | heating plate | 90 | 30 | | | |
| decreasing vacuum | 5 | 17 | stable | 1410 | 30 | | | |
| stable vacuum | 10 | 17 | | | | | | |
| decreasing vacuum | 5 | 14 | | | | | | |
| decreasing vacuum | 5 | 12 | | | | | | |
| decreasing vacuum | 5 | 10 | | | | | | |
| decreasing vacuum | 5 | 8 | | | | | | |
| stable vacuum | 5 | 8 | | | | | | |
| decreasing vacuum | 5 | 6 | | | | | | |
| stable vacuum | 25 | 6 | | | | | | |
| decreasing vacuum | 5 | 4 | | | | | | |
| stable vacuum | 5 | 4 | | | | | | |
| decreasing vacuum | 5 | 2 | | | | | | |
| stable vacuum | 5 | 2 | | | | | | |
| decreasing vacuum | 5 | 1.3 | | | | | | |
| stable vacuum | 95 | 1.3 | | | | | | |
| high vacuum | 1310 | / | | | | | | |

TABLE 10

Vitrification of PA IB88: HR 4.6%

| | Pressure | | Dryer | | | | |
|---|---|---|---|---|---|---|---|
| | | | Shelf Temperature | | Trap Temperature | | |
| step | Tps Min | Pressure mbar | step | Tps Min | Temp °c. | step | Tps Min | Temp °c. |
| decreasing vacuum | 0 | 490 | refrig. plates | 0 | 4 | refrig. trap | 25 | -70 |
| decreasing vacuum | 5 | 22 | stable | 10 | 4 | | | |
| decreasing vacuum | 5 | 17 | heating plate | 85 | 30 | | | |
| stable vacuum | 10 | 17 | stable | 1030 | 30 | | | |
| decreasing vacuum | 5 | 12 | | | | | | |
| stable vacuum | 5 | 12 | | | | | | |
| decreasing vacuum | 5 | 10 | | | | | | |
| decreasing vacuum | 5 | 8 | | | | | | |
| decreasing vacuum | 5 | 6 | | | | | | |
| stable vacuum | 40 | 6 | | | | | | |
| decreasing vacuum | 5 | 4 | | | | | | |
| stable vacuum | 5 | 4 | | | | | | |
| decreasing vacuum | 5 | 2 | | | | | | |
| stable vacuum | 5 | 2 | | | | | | |
| decreasing vacuum | 5 | 1 | | | | | | |
| stable vacuum | 150 | 1 | | | | | | |
| high vacuum | 865 | / | | | | | | |

TABLE 11

Vitrification Pasteurella 50/50 S54 + S (325 g/L): HR 5.5%;
Vitrification Pasteurella 50/50 F2 + S (325 g/L): HR 6.1%

| | Pressure | | Dryer | | | | |
|---|---|---|---|---|---|---|---|
| | | | Shelf Temperature | | Trap Temperature | | |
| step | Tps Min | Pressure mbar | step | Tps Min | Temp °c. | step | Tps Min | Temp °c. |
| decreasing vacuum | 0 | 715 | refrig. plates | 0 | 4 | refrig. trap | 30 | -70 |
| decreasing vacuum | 5 | 30 | stable | 15 | 4 | | | |
| decreasing vacuum | 5 | 18 | heating plate | 75 | 30 | | | |
| stable vacuum | 10 | 18 | stable | 1455 | 30 | | | |
| decreasing vacuum | 5 | 14 | | | | | | |
| stable vacuum | 5 | 14 | | | | | | |
| decreasing vacuum | 5 | 12 | | | | | | |
| decreasing vacuum | 5 | 10 | | | | | | |
| stable vacuum | 5 | 10 | | | | | | |
| decreasing vacuum | 5 | 8 | | | | | | |

TABLE 11-continued

Vitrification Pasteurella 50/50 S54 + S (325 g/L): HR 5.5%;
Vitrification Pasteurella 50/50 F2 + S (325 g/L): HR 6.1%

| | Pressure | | Dryer | | | | |
|---|---|---|---|---|---|---|---|
| | | | | Shelf Temperature | | Trap Temperature | |
| step | Tps Min | Pressure mbar | step | Tps Min | Temp °c. | step | Tps Min | Temp °c. |
| stable vacuum | 10 | 8 | | | | | |
| decreasing vacuum | 5 | 6 | | | | | |
| stable vacuum | 30 | 6 | | | | | |
| decreasing vacuum | 5 | 4 | | | | | |
| decreasing vacuum | 5 | 2 | | | | | |
| decreasing vacuum | 5 | 1 | | | | | |
| stable vacuum | 1015 | 1 | | | | | |
| high vacuum | 460 | / | | | | | |

TABLE 12

Vitrification Avibacterium 50/50 S54 + S (325 g/L): HR 4.8%;
Vitrification Avibacterium 50/50 F2 + S (325 g/L): HR 6%

| | Pressure | | Dryer | | | | |
|---|---|---|---|---|---|---|---|
| | | | | Shelf Temperature | | Trap Temperature | |
| step | Tps Min | Pressure mbar | step | Tps Min | Temp °c. | step | Tps Min | Temp °c. |
| decreasing vacuum | 0 | 404 | refrig. plates | 0 | 4 | refrig. trap | 15 | −70 |
| decreasing vacuum | 5 | 23 | stable | 15 | 4 | | | |
| decreasing vacuum | 5 | 17 | heating plate | 80 | 30 | | | |
| stable vacuum | 10 | 17 | stable | 1705 | 30 | | | |
| decreasing vacuum | 5 | 14 | | | | | |
| stable vacuum | 5 | 14 | | | | | |
| decreasing vacuum | 5 | 12 | | | | | |
| decreasing vacuum | 5 | 10 | | | | | |
| stable vacuum | 5 | 10 | | | | | |
| decreasing vacuum | 5 | 8 | | | | | |
| stable vacuum | 15 | 8 | | | | | |
| decreasing vacuum | 5 | 6 | | | | | |
| stable vacuum | 20 | 6 | | | | | |
| decreasing vacuum | 5 | 4 | | | | | |
| decreasing vacuum | 5 | 2 | | | | | |
| decreasing vacuum | 5 | 1 | | | | | |
| stable vacuum | 1255 | 1 | | | | | |
| high vacuum | 385 | / | | | | | |

TABLE 13

Vitrification of vCP2017 50/50 S11 + S 325 g/L: HR 7.5%;
Vitrification of vCP2017 50/50 F2 + S 325 g/L: HR 7.1%

| | Pressure | | Dryer | | | | |
|---|---|---|---|---|---|---|---|
| | | | | Shelf Temperature | | Trap Temperature | |
| step | Tps Min | Pressure mbar | step | Tps Min | Temp °c. | step | Tps Min | Temp °c. |
| decreasing vacuum | 0 | 372 | refrig. plates | 0 | 4 | refrig. trap | 15 | −70 |
| decreasing vacuum | 5 | 18 | stable | 10 | 4 | | | |
| decreasing vacuum | 5 | 17 | heating plate | 75 | 30 | | | |
| stable vacuum | 10 | 17 | stable | 1625 | 30 | | | |
| decreasing vacuum | 5 | 13 | | | | | |
| decreasing vacuum | 5 | 10 | | | | | |
| decreasing vacuum | 5 | 8 | | | | | |
| decreasing vacuum | 5 | 6 | | | | | |
| stable vacuum | 30 | 6 | | | | | |
| decreasing vacuum | 5 | 4 | | | | | |
| decreasing vacuum | 5 | 2 | | | | | |
| decreasing vacuum | 5 | 1 | | | | | |
| stable vacuum | 170 | 1 | | | | | |
| high vacuum | 1455 | / | | | | | |

TABLE 14

Vitrification of ERN: HR 4.1%

| | Pressure | | Dryer | | | | |
|---|---|---|---|---|---|---|---|
| | | | | Shelf Temperature | | Trap Temperature | |
| step | Tps Min | Pressure mbar | step | Tps Min | Temp °c. | step | Tps Min | Temp °c. |
| decreasing vacuum | 0 | 372 | refrig. plates | 0 | 4 | refrig. trap | 10 | −70 |
| decreasing vacuum | 5 | 17 | stable | 15 | 4 | | | |
| decreasing vacuum | 5 | 15 | heating plate | 75 | 30 | | | |
| stable vacuum | 10 | 15 | stable | 1625 | 30 | | | |
| decreasing vacuum | 5 | 12 | | | | | |
| decreasing vacuum | 5 | 10 | | | | | |
| decreasing vacuum | 5 | 8 | | | | | |
| decreasing vacuum | 5 | 6 | | | | | |
| stable vacuum | 50 | 6 | | | | | |
| decreasing vacuum | 5 | 4 | | | | | |
| decreasing vacuum | 5 | 2 | | | | | |
| decreasing vacuum | 5 | 1 | | | | | |

TABLE 14-continued

Vitrification of ERN: HR 4.1%

| step | Pressure Tps Min | Pressure sure mbar | Dryer Shelf Temperature Tps step | Dryer Shelf Temperature Min | Dryer Shelf Temperature Temp ° c. | Dryer Trap Temperature Tps step | Dryer Trap Temperature Min | Dryer Trap Temperature Temp ° c. |
|---|---|---|---|---|---|---|---|---|
| stable vacuum | 135 | 1 | | | | | | |
| high vacuum | 1415 | / | | | | | | |

Example 2: Stability Studies after Freeze-Drying

EURICAN (CDV & PI2) was subjected to Lyophilization, Vitrification (according to method disclosed above), or Prilling. The Tables provide summary details for the tested immunological formulations.

TABLE 15

Nine-month stability study, RECOMBITEK ® (EURICAN, Merial)

Titer in log10CCID50/ml Cycle

| Valence | EURICAN Lyophilization CDV | EURICAN Lyophilization PI2 | EURICAN Vitrification CDV | EURICAN Vitrification PI2 | EURICAN Prilling CDV | EURICAN Prilling PI2 |
|---|---|---|---|---|---|---|
| Target formulation | 0.48 ml | 6.73 | 0.48 ml | 6.73 | 0.48 ml | 6.73 |
| T 0 | 5.41 | 6.14 | 5.88 | 6.47 | 5.07 | 6.02 |
| T 3 months | 5.33 | 5.95 | 5.71 | 6.47 | 4.72 | 5.9 |
| T 6 months | 5.4 | 5.99 | 5.78 | 6.39 | 4.68 | 5.6 |
| T 9 months | 5.39 | 5.71 | 5.76 | 6.6 | 4.69 | 5.88 |

TABLE 16

Six-month stability study, vCP97 (canarypox-vectored FeLV antigens, Merial FeLV ®)

Titer in log10CCID50/ml

| | Lyophilization in stabilizer S11 | Lyophilization in stabilizer F02 | Vitrification in stabilizer S11 | Vitrification in stabilizer F02 |
|---|---|---|---|---|
| Target Formulation | 8.1 | 8.1 | 8.1 | 8.1 |
| T 0 | 7.91 | 7.87 | 8.2 | 7.94 |
| T 6 months | 7.56 | 7.6 | 7.48 | 7.65 |

TABLE 17

Six-month stability study, vCP2017 (canarypox-vectored WNV, Merial RECOMBITEK ® WNV)

Titer in log10CCID50/ml

| | Lyophilization in stabilizer S11 | Lyophilization in stabilizer F02 | Vitrification in stabilizer S11 | Vitrification in stabilizer F02 |
|---|---|---|---|---|
| Target Formulation | 7.5 | 7.5 | 7.5 | 7.5 |
| T 0 | 6.87 | 6.93 | 7.07 | 7 |
| T 6 months | 6.34 | 6.52 | 6.9 | 6.53 |

TABLE 18

Three-month stability study, attenuated avibacterium

| | Pasteurella Lyoph. in stab. 54 | Pasteurella Lyoph. in stab. F02 | Pasteurella Vitrif. in stab. 54 | Pasteurella Vitrif. in stab. F02 | Avibacterium Lyoph. in stab. 54 | Avibacterium Lyoph. in stab. F02 | Avibacterium Vitrif. in stab. 54 | Avibacterium Vitrif. in stab. F02 |
|---|---|---|---|---|---|---|---|---|
| T 0 before lyoph. OR vitrif. | 9.73 | 9.73 | 9.45 | 9.45 | 8.97 | 8.97 | 9.01 | 9.01 |
| T 0 after lyoph. OR vitrif. | 8.8 | 8.88 | 7.83 | 7.82 | 8.15 | 8.15 | 4.76 | 4.58 |
| T 1 week | 8.8 | 8.88 | 7.84 | 7.83 | / | / | / | / |
| T 1 months | / | / | / | / | 7.58 | 7.87 | 5.56 | 5.63 |
| T 3 months | 8.76 | 8.66 | 7.78 | 7.18 | / | / | / | / |

TABLE 19

Eighteen-month stability study, MAREK's Disease, vitrified according to the instant disclosure

| | Titer in log10PFU/ml | | |
|---|---|---|---|
| | 091023-1<br>S32 50%/50% PA | 091023-4<br>S32 1/3-2/3 PA | 091126-8<br>S32 + Sac 30%/70% PA |
| T 0 | 4.75 | 4.65 | 4.88 |
| T 6 months | 5.11 | 5.07 | 5.25 |
| T 12 months | 4.05 | 3.96 | 4.37 |
| T 18 months | 4.17 | 4.05 | ??? |

Infectious Bursal disease (coronavirus), Newcastle Disease Virus (NDV), *Leishmania* KSAC polypeptide, and Chicken Embryonic Fibroblast (CEF) cells were also successfully vitrified according to the method of the instant disclosure.

Example 4: Testing Vaccines in Dogs

The vitrified vaccines described in Example 1 are administered to animals after rehydration in sterile injectable water. Four specific pathogen-free (SPF) dogs aged 3 to 5 months old and 4 conventional dogs aged 3 to 5 months old, are randomly allocated into 4 groups of two animals, wherein each group had one SPF dog and one conventional dog. For each group, two dogs are immunized subcutaneously on day 0 with a double dose (2 ml) of their corresponding vitrified/stabilized vaccine. On day 14, dogs are immunized subcutaneously with a single dose (1 ml) of the same stabilized vaccine. Immediate local reactions and immediate general reactions, rectal temperatures, local reactions, general reactions and clinical symptoms are observed. No local or general reaction following administration are observed. Therefore, the safety of the vitrified/stabilized vaccines appears to be high.

Having thus described in detail preferred embodiments of the present invention, it is to be understood that the invention defined by the appended claims is not to be limited by particular details set forth in the above description as many apparent variations thereof are possible without departing from the spirit or scope thereof.

What is claimed is:

1. A process for vitrifying biological material comprising the steps of:
   (a) formulating a liquid biological preparation, wherein the liquid biological preparation comprises at least one active biologic ingredient selected from RNA and DNA viruses; and at least one stabilizer, wherein the at least one stabilizer comprises: 1) a bulking agent consisting of dextran, present in an amount of about 6% to about 10% w/v of the stabilizer: 2) one of the following combinations of sugars: glucose+raffinose; glucose+fructose; glucose+galactose; or glucose+sucrose, wherein the glucose is present in an amount of about 1% to about 5% w/v of the stabilizer and 3) optionally aspartic acid: wherein the stabilizer is capable of reducing or eliminating cryogenic damage to the biologic ingredient;
   (b) adding a portion of the liquid biological preparation of step (a) to at least one vial;
   (c) loading the at least one vial into a temperature-controlled container, wherein the temperature of the temperature-controlled container is between −15° C. and 10° C.; and
   (d) reducing the moisture content of the biological preparation to less than about 5% by weight by controlled changes in pressure and temperature, comprising the following steps in the following order:
      1) reducing pressure from about 10-30 mbar to about 5 mbar, over about 5-15 minutes, then holding the pressure at about 5 mbar for about 40-50 minutes;
      2) reducing pressure from about 5 mbar to about 3 mbar, over about 5-10 minutes, then holding the pressure at about 3 mbar for about 10-40 minutes; and
      3) reducing pressure from about 3 mbar to about 1.5-2 mbar, over about 5-10 minutes, then holding the pressure at about 1.5-2 mbar for about 5-160 minutes;
   thereby reducing the moisture content of the biological preparation to less than about 5% by weight, and thereby vitrifying the biological material, and wherein the one or more biologic ingredients remains at least 85% viable for at least a year after vitrification, thereby the one or more biologic ingredients is stabilized.

2. The process of claim 1, wherein reducing the moisture content of the biological preparation further comprises the steps of:
   (e) reducing the pressure of the temperature-controlled container to between about 0.5 and about 2.0 mbars, and maintaining a constant pressure until foaming has completed;
   (f) reducing the pressure of the temperature-controlled container to between about 5 μbar and about 100 μbar while maintaining the temperature of the temperature-controlled container at about 30° C. for about 400 to about 2400 or more minutes, until a moisture content of between about 0.5% to about 15% is obtained; and
   (g) completing the vitrification process by stoppering the at least one vial while it is within the temperature-controlled container and
   wherein the at least one active biologic ingredient comprises a live attenuated virus.

3. The process of claim 2, wherein the live virus is selected from canine distemper virus (CDV), canine parainfluenza virus type 2 (PI2), and a combination thereof.

4. The process of claim 2, wherein the live attenuated virus is selected from canarypox, Marek's disease virus, infectious bronchitis, west nile virus (WNV) and feline leukemia virus (FeLV).

5. The process of claim 1, wherein the biological preparation comprises at least one adjuvant.

6. The process of claim 1, wherein the vitrified biological material is stable at 4° C. for at least one year.

7. The process of claim 1, wherein the vitrified biological material is stable at −20° C. and −80° C. for at least one year.

8. A process for preparing a vitrified biological preparation comprising the steps of:
   (a) adding to an active biologic ingredient, which is selected from RNA viruses and DNA viruses, stabilizers, which reduce or eliminate damage induced by subjecting the biologic ingredient to cryogenic preservation means, and optionally adding one or more adjuvants; and wherein the stabilizer comprises dextran, present in an amount of about 6% to about 10% w/v of the stabilizer, and one or more of the following combinations of sugars: glucose+raffinose; glucose+ fructose; glucose+galactose; or glucose+sucrose, wherein the glucose is present in an amount of about 1% to about 5% w/v of the stabilizer: thereby preparing a biological preparation;

(b) filling vials with the biological preparation of step (a);

(c) loading of vials into temperature-controlled container, wherein the temperature is between −15° C. and 10° C.;

(d) reducing the air pressure of the temperature-controlled container until a pressure within the range of 15-30 mbars is obtained;

(e) maintaining the pressure obtained during step (d) for between 5 and 20 minutes, to allow the temperature of the preparation to stabilize and to allow volatile gases to be released from the biological preparation, wherein the container temperature remains at about 4° C. to about 6° C. during this step;

(f) decreasing the container air pressure to about 1.5 to about 2.5 mbars using the following steps, in the following order;

1) reducing pressure from about 15-30 mbar to about 5 mbar, over about 5-15 minutes, then holding pressure at about 5 mbar for about 40-50 minutes;

2) reducing pressure from about 5 mbar to about 3 mbar, over about 5-10 minutes, then holding pressure at about 3 mbar for about 10-40 minutes;

3) reducing pressure from about 3 mbar to about 1.5-2.5 mbar, over about 5-10 minutes;

(g) maintaining the pressure of step (f)(3) for about 5 to about 160 minutes, which allows the biological preparation to become more concentrated;

(h) increasing the temperature of the container from negative to positive temperature over the course of between 45 and 85 minutes, and holding the pressure constant until reaching about 10° C. to about 20° C.;

(i) reducing container air pressure to accelerate the concentration, and until the container temperature reaches and maintains about 30° C. for about 30 minutes to about 90 minutes;

(j) further reducing pressure to between about 0.5 and about 4.0 mbars, or about 1 mbar, and then maintaining constant pressure until foaming has completed;

(k) further reducing pressure to between about 5 µbar and about 100 µbar, while maintaining the temperature at about 30° C. for about 400 to about 2400 or more minutes, until the desired moisture of between about 0.5% to about 15% is obtained;

(l) stoppering the vials while in the freeze-dryer container, thereby completing the vitrification process.

9. The process of claim 8, wherein the active biologic ingredient is a live virus.

10. The process of claim 9, wherein active biologic ingredient is a live attenuated virus.

11. The process of claim 9, wherein the virus is canine distemper virus (CDV), canine parainfluenza virus type 2 (PI2), or combinations thereof.

12. The process of claim 9, wherein the attenuated virus is canarypox, Marek's disease virus, infectious bursal disease virus, west nile virus (WNV) or feline leukemia virus (FeLV).

13. The process of claim 1, wherein the aspartic acid is present, and is present in an amount of about 0.20% to about 0.50% w/v of the stabilizer.

14. The process of claim 13, wherein the aspartic acid is present in an amount of about 0.20% w/v of the stabilizer.

15. The process of claim 13, wherein the aspartic acid is present in an amount of about 0.40% w/v of the stabilizer.

16. The process of claim 13, wherein the aspartic acid is present in an amount of about 0.50% w/v of the stabilizer.

17. The process of claim 2, wherein the aspartic acid is present, and is present in an amount of about 0.20% to about 0.50% w/v of the stabilizer.

18. The process of claim 17, wherein the aspartic acid is present, and is present in an amount of about 0.20% w/v of the stabilizer.

19. The process of claim 17, wherein the aspartic acid is present, and is present in an amount of about 0.40% w/v of the stabilizer.

20. The process of claim 17, wherein the aspartic acid is present, and is present in an amount of about 0.50% w/v of the stabilizer.

* * * * *